(12) United States Patent
el Kaliouby et al.

(10) Patent No.: US 10,143,414 B2
(45) Date of Patent: Dec. 4, 2018

(54) SPORADIC COLLECTION WITH MOBILE AFFECT DATA

(71) Applicant: Affectiva, Inc., Waltham, MA (US)

(72) Inventors: Rana el Kaliouby, Milton, MA (US); Daniel Bender, Cambridge, MA (US); Evan Kodra, Waltham, MA (US); Oliver Ernst Nowak, Medford, MA (US); Richard Scott Sadowsky, Sturbridge, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 14/961,279

(22) Filed: Dec. 7, 2015

(65) Prior Publication Data

US 2016/0081607 A1    Mar. 24, 2016

Related U.S. Application Data

(63) Continuation-in-part of application No. 14/064,136, filed on Oct. 26, 2013, now Pat. No. 9,204,836, and
(Continued)

(51) Int. Cl.
*G06K 9/00* (2006.01)
*A61B 5/16* (2006.01)
(Continued)

(52) U.S. Cl.
CPC ............ *A61B 5/165* (2013.01); *A61B 5/0022* (2013.01); *A61B 5/0531* (2013.01);
(Continued)

(58) Field of Classification Search
CPC ........... G06K 9/00275; G06K 9/00281; G06K 9/0028; G06K 9/00295; G06K 9/00302;
(Continued)

(56) References Cited

U.S. PATENT DOCUMENTS 3,034,500 A    5/1962  Backster, Jr.
3,548,806 A    12/1970 Fisher
(Continued)

FOREIGN PATENT DOCUMENTS

JP            08115367        7/1996
KR    10-2005-0021759 A    3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Wesley J Tucker
(74) *Attorney, Agent, or Firm* — Adams Intellex, PLC

(57) ABSTRACT

An individual can exhibit one or more mental states when reacting to a stimulus. A camera or other monitoring device can be used to collect, on an intermittent basis, mental state data including facial data. The mental state data can be interpolated between the intermittent collecting. The facial data can be obtained from a series of images of the individual where the images are captured intermittently. A second face can be identified, and the first face and the second face can be tracked.

29 Claims, 14 Drawing Sheets

Related U.S. Application Data a continuation-in-part of application No. 13/153,745, filed on Jun. 6, 2011, now abandoned, and a continuation-in-part of application No. 14/796,419, filed on Jul. 10, 2015, now abandoned, said application No. 14/796,419 is a continuation-in-part of application No. 14/460,915, filed on Aug. 15, 2014, said application No. 14/796,419 is a continuation-in-part of application No. 13/153,745, filed on Jun. 6, 2011, now abandoned.

(60) Provisional application No. 62/128,974, filed on Mar. 5, 2015, provisional application No. 62/217,872, filed on Sep. 12, 2015, provisional application No. 62/222,518, filed on Sep. 23, 2015, provisional application No. 61/719,383, filed on Oct. 27, 2012, provisional application No. 61/747,651, filed on Dec. 31, 2012, provisional application No. 61/747,810, filed on Dec. 31, 2012, provisional application No. 61/793,761, filed on Mar. 15, 2013, provisional application No. 61/790,461, filed on Mar. 15, 2013, provisional application No. 61/789,038, filed on Mar. 15, 2013, provisional application No. 61/798,731, filed on Mar. 15, 2013, provisional application No. 61/844,478, filed on Jul. 10, 2013, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 62/023,800, filed on Jul. 11, 2014, provisional application No. 62/047,508, filed on Sep. 8, 2014, provisional application No. 62/082,579, filed on Nov. 20, 2014, provisional application No. 61/867,007, filed on Aug. 16, 2013, provisional application No. 61/924,252, filed on Jan. 7, 2014, provisional application No. 61/916,190, filed on Dec. 14, 2013, provisional application No. 61/927,481, filed on Jan. 15, 2014, provisional application No. 61/953,878, filed on Mar. 16, 2014, provisional application No. 61/972,314, filed on Mar. 30, 2014.

(51) Int. Cl.
| | | |
|---|---|---|
| *G06K 9/62* | (2006.01) | |
| *A61B 5/053* | (2006.01) | |
| *A61B 5/00* | (2006.01) | |
| *G06F 19/00* | (2018.01) | |
| *A61B 5/01* | (2006.01) | |
| *A61B 5/0205* | (2006.01) | |
| *A61B 5/024* | (2006.01) | |
| *A61B 5/08* | (2006.01) | |
| *A61B 5/11* | (2006.01) | |
| *G06Q 30/02* | (2012.01) | |

(52) U.S. Cl.
CPC ...... *G06F 19/3418* (2013.01); *G06F 19/3481* (2013.01); *G06K 9/00255* (2013.01); *G06K 9/00281* (2013.01); *G06K 9/00288* (2013.01); *G06K 9/00302* (2013.01); *G06K 9/6267* (2013.01); *A61B 5/0077* (2013.01); *A61B 5/01* (2013.01); *A61B 5/02055* (2013.01); *A61B 5/02405* (2013.01); *A61B 5/0533* (2013.01); *A61B 5/08* (2013.01); *A61B 5/11* (2013.01); *A61B 5/6898* (2013.01); *A61B 5/72* (2013.01); *A61B 2562/0219* (2013.01); *G06Q 30/0271* (2013.01)

(58) Field of Classification Search
CPC .......... G06K 9/00308; G06K 9/00315; G06K 9/00335; G06K 9/00342; G06K 9/00348; G06K 9/00355; G06K 9/00362; G06K 9/00241

See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A * | 7/1997 | Ron .................. A61B 5/16 600/23 |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |

(56) References Cited

U.S. PATENT DOCUMENTS

| | | |
|---|---|---|
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,747,801 B2 | 6/2010 | Han et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1* | 11/2002 | Eshelman ............ G06Q 50/22 340/573.1 |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1* | 8/2005 | Matsugu ............... A61B 5/16 600/301 |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1* | 11/2008 | Kurtz ................. A61B 3/10 382/128 |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0149721 A1* | 6/2009 | Yang .................. A61B 5/0002 600/301 |
| 2009/0150919 A1 | 6/2009 | Lee et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0324491 A1 | 12/2012 | Bathiche et al. |
| 2013/0023337 A1 | 1/2013 | Bowers et al. |
| 2013/0116587 A1 | 5/2013 | Sornmo et al. |
| 2013/0197409 A1 | 8/2013 | Baxter et al. |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming HE, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

(56) References Cited

OTHER PUBLICATIONS

Albiol, Alberto, et al. "Face recognition using HOG-EBGM." Pattern Recognition Letters 29.10 (2008): 1537-1543.

* cited by examiner

SPORADIC COLLECTION WITH MOBILE AFFECT DATA

RELATED APPLICATIONS

This application claims the benefit of U.S. provisional patent applications "Viewership Analysis Based on Facial Evaluation" Ser. No. 62/128,974, filed Mar. 5, 2015, "Mental State Event Signature Usage" Ser. No. 62/217,872, filed Sep. 12, 2015, and "Image Analysis In Support of Robotic Manipulation" Ser. No. 62/222,518, filed Sep. 23, 2015. This application is also a continuation-in-part of U.S. patent application "Sporadic Collection of Mobile Affect Data" Ser. No. 14/064,136, filed Oct. 26, 2013, which claims the benefit of U.S. provisional patent applications "Sporadic Collection of Mobile Affect Data" Ser. No. 61/719,383, filed Oct. 27, 2012, "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013. This application is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. This application is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based on Facial Evaluation" Ser. No. 62/128,974, filed Mar. 5, 2015; the application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011; the application is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014 and is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states and more particularly to analysis of sporadic collection with mobile affect data.

BACKGROUND

People increasingly spend a tremendous amount of time interacting with computers; this interaction includes a copious amount of media consumption using these computers. This interaction may be for many different reasons such as education, entertainment, social media interaction, document creation, and gaming, to name a few.

In some cases, the human-computer interaction can take the form of a person performing a task using a software-based tool running on a computer. Examples include filling out a tax form, creating a document, editing a video, and/or doing one or more of the numerous other activities performable by a modern computer. The person can find the execution of certain activities interesting or even exciting, and may be surprised at how easy it is to perform the activity. The person may become excited, happy, or content as he or she performs such an interesting or exciting activity. On the other hand, the person can find some activities difficult to perform, and may become frustrated or even angry with the computer or software tool. In some cases, users are surveyed in an attempt to determine where a computer or computer program may be functioning well, and where it may need improvement. However, such survey results are often unreliable because the surveys are often completed well after the activity was performed. In addition, survey participation rates may be low, and people may not provide accurate and honest answers to the survey.

In other cases of human-computer interaction, the person is using a software tool to accomplish a task, but instead may be consuming computer-accessed content or media such as news, pictures, music, or video. Currently, while or after consuming computer-driven content, viewers may self-rate the media to communicate personal preferences. In some cases, viewers may enter a specific number of stars corresponding to a level of like or dislike, while in other cases, users may be asked to answer a list of questions. While this system of evaluation is a helpful metric to evaluate media and other products or services, such evaluation may be tedious and challenging. Thus, in many cases, this type of subjective evaluation is neither a reliable nor practical way to evaluate personal response to media. Recommendations based on such a system of star rating or other self-reporting are imprecise, subjective, unreliable, and are further limited by sample size: often, only a small number of viewers actually rate the media they have consumed.

SUMMARY

A user frequently interacts with computers, mobile devices, and handheld devices. Any of the interactions with the myriad of devices can entail any of a variety of tasks and/or activities. A manifestation of the user-device interactions can be moods, mental states, and so on. A given mental state can be presented in many ways including facial expressions, electrodermal activity, movements (voluntary and involuntary), or other externally detectable manifestations. A camera and other monitoring devices can be used to capture one or more of the externally detectable manifestations of the user's mental state, but there may be conditions where the monitoring device may not be able to detect the manifestation continually. Thus, various methods, computer program products, apparatus, and systems are described wherein mental state data is collected on an intermittent basis, analyzed, and an output rendered based on the analysis of the mental state data. A computer-implemented method for mental state analysis is disclosed comprising: collecting mental state data of an individual on an intermittent basis; obtaining analysis of the mental state data on the individual; and rendering an output based on the analysis of the mental state data. In embodiments, the method includes interpolation of mental state data or mental state analysis in between the collecting which is intermittent. In some embodiments, collecting other mental state data from the individual, including electrodermal activity, can occur on a continuous basis.

In embodiments, a computer-implemented method for mental state analysis comprises: collecting mental state data of an individual on an intermittent basis wherein the mental state data includes facial data; interpolating mental state data in between the collecting which is intermittent; obtaining analysis, using one or more processors, of the mental state data on the individual; and rendering an output based on the analysis of the mental state data. In some embodiments, a computer program product is embodied in a non-transitory computer readable medium for mental state analysis, the computer program product comprising: code for collecting mental state data of an individual on an intermittent basis wherein the mental state data includes facial data; code for interpolating mental state data in between the collecting which is intermittent; code for obtaining analysis, using one or more processors, of the mental state data on the individual; and code for rendering an output based on the analysis of the mental state data. In embodiments, a system for mental state analysis comprises: a memory for storing instructions; one or more processors attached to the memory wherein the one or more processors are configured to: collect mental state data of an individual on an intermittent basis wherein the mental state data includes facial data; interpolate mental state data in between the collecting which is intermittent; obtain analysis, using one or more processors, of the mental state data on the individual; and render an output based on the analysis of the mental state data.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
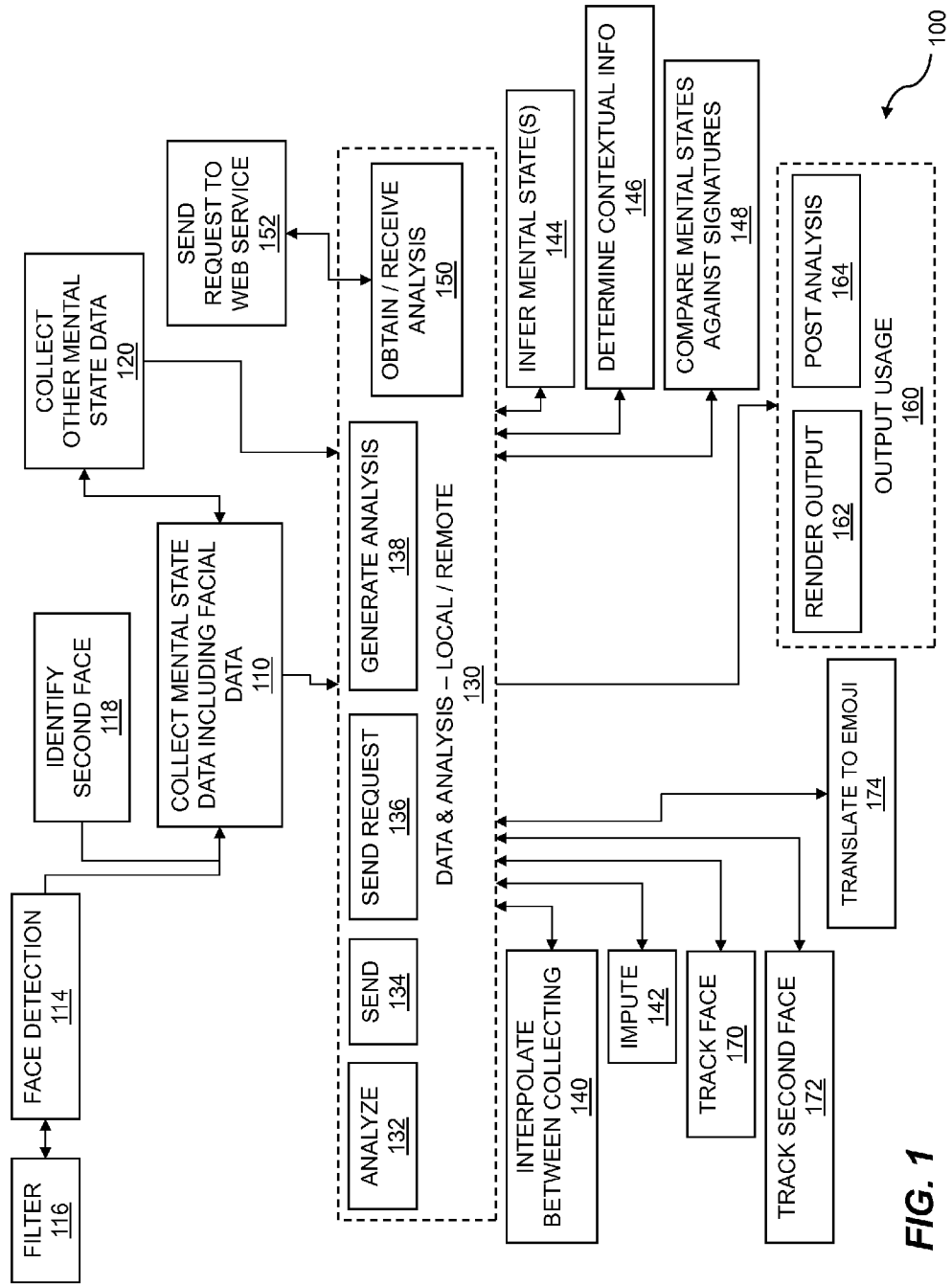
FIG. 1 is a flow diagram for sporadic collection.

As a user interacts with a computer, the user's mental state can provide valuable insight into the nature of the human-computer interaction. The mental state of the user can include such emotions as enjoyment, happiness, anger, sadness, stress, frustration, confusion, disappointment, hesitation, cognitive overload, fear, exhaustion, focus, engagement, attention, boredom, exploration, confidence, trust, delight, satisfaction, excitement, happiness, contentment, or one of many other human emotions. Understanding a user's mental state as he or she interacts with the computer may be valuable for a variety of reasons, such as determining which aspects of a computer program may be working well and which aspects need improvement, determining aspects of a computer game that may be too difficult or two easy for some users, measuring effectiveness of advertisements, determining which parts of a video most please a specific user, or determining a user's preferences in order to better suggest what other media, games, or applications the specific user may find appealing, just to name a few.

While consuming media, the user may exhibit physical manifestations of his or her mental state, such as facial expressions, physiological reactions, and movement. Sensors coupled to a computer—in some embodiments, the same computer the user is interacting with; in other embodiments, one or more other computers—may be able to detect, capture, and/or measure one or more external manifestations of the user's mental state. For example, a still camera may be able to capture images of the user's face, a video camera may be able to capture images of the user's movements, a heart rate monitor may be able to measure the user's heart rate, a skin resistance sensor may be able to detect changes in the user's galvanic skin response, and an accelerometer may be able to measure such movements as gestures, foot tapping, or head tilts, to name a few.

Depending on the user and/or the sensor, however, it may not be possible to continuously capture all of the manifestations of mental states under observation. For example, if the user looks away from the camera, it may not be possible to capture an image of their face until they look back at the camera. As a further example, a skin resistance sensor embedded in an armrest of the user's chair can only measure a galvanic skin response if the user's arm is resting on the armrest. In other cases, it may be possible to continuously capture the data from a sensor, but it may not be practical or desirable to do so due to the volume of data capture, or due to the relative slowness of measurable change that may be expected from the manifestation of a particular mental state.

To accommodate such circumstances, data from at least some of the sensors which measure manifestations of mental state (which may also be referred to as mental state data), such as data from a camera, biosensor, or accelerometer, may be captured, collected, and/or stored, on an intermittent basis. The intermittent basis may be sporadic, opportunistic, periodic, random, or any other non-continuous basis. Data from the sensors may be captured from the sensor based on the ability of the sensor to capture valid data, based on the usefulness of the data captured from the sensor, based on a schedule, or based on indications from other sensors, depending on the embodiment. For example, a skin resistance meter may only provide collectable data if it detects that the user's skin is in contact with the meter. Similarly, an image from a camera may, perhaps, only be saved for further analysis if some form of pre-processing detects that the user's face is visible in the image, or a video of a user's body (used for movement analysis) may be taken only when triggered by a change in heart rate detected by a heart rate monitor. A wide variety of techniques may be used to intermittently collect, capture, and/or store sensor data related to a mental state of an individual. In one example, when a pattern of motion predicts a high probability of a physiological condition occurring, other sensors may be activated to provide greater contextual information and increase predictive abilities.

Once the intermittent sensor data has been collected, an analysis of the mental state data collected from the sensors is obtained. The analysis may take place on the computer with which the user is interacting, the computer(s) that captured the sensor data, and/or from one or more other computers that may be local or remote to the user. The analysis may provide mental states of the user over time based on the sensor data. In some cases, the mental state of the user may be estimated for the periods where data from one or more sensors was not collected.

After the analysis of the mental state data has been obtained, an output is rendered based on the analysis of the mental state data. The rendered output may include text, icons, pictures, graphs, binary data, or any other form or output that may be interpreted by a person or another computer, depending on the embodiment. In at least one embodiment, the rendered output may include a graph showing the prevalence of a particular mental state over time. In some embodiments, the rendered output may include an icon that changes based on the user's mental state. In some embodiments, the rendered output may include a file containing numerical data based on the analysis obtained. In embodiments, the sporadic collection of mental state data can be used in evaluating the well-being of a person or in the generation of a personal emotional profile.

FIG. 1 is a flow diagram for sporadic collection. The flow 100 includes a computer-implemented method for sporadic collection of mental state data and mental state analysis with mobile affect data. The flow 100 includes collecting mental state data of an individual on an intermittent basis where the mental state data includes facial data 110. Any non-continuous collection of mental state data can be considered collection on an intermittent basis. In some embodiments, the intermittent basis can be opportunistic, where the intermittent basis can be either sporadic or occasional. The intermittent basis can include the capture of images at time random intervals, at times when the individual takes certain actions, at times when the user happens to look in the direction of a camera, and so on. The collecting mental state data can be based on image analysis of the facial data. The facial data can be obtained from a series of images of the individual where the series of images can include a series of still images, frames extracted from a video, etc. In other embodiments, the intermittent basis can be periodic, and can occur on a regular schedule. For example, one or more images of the user can be collected once every 30 seconds. In some embodiments, the intermittent basis can be a combination of occasional and periodic collection. For example, the collecting can include collecting mental state data once every minute plus additional data collection each time the user performs some act. The act that the user can perform can include clicking a mouse button, hitting a particular key such as the 'Enter' key on a computer keyboard, touching or swiping a screen on a handheld device, tilting a handheld device, and so on. The collecting can be accomplished for one or more types of mental state data. In embodiments, the mental state data that can be collected can include facial data. In addition to collecting the mental state data on an intermittent basis, the flow 100 can further include collecting other mental state data 120 from the individual on a continuous basis. In embodiments, the other mental state data can include electrodermal activity data, heart rate, heart rate variability, skin temperature, and so on.

Many different types of mental state data can be collected. For example, the mental state data can include one or more of a group including physiological data, facial data, accelerometer data, and so on. Any appropriate sensors can be used for the collection of mental state data. The collecting of the mental state data can be accomplished using a variety of different sensors that can be chosen depending on the type of mental state data being collected. In at least one embodiment, a camera coupled to a computer or other portable or handheld electronic device can be used to capture mental state data, where the mental state data can include facial data such as facial expressions. Facial expressions that can be used to infer mental state data can include one or more of smiles, laughter, smirks, grimaces, etc. The mental state data also can include one or more of head position, up/down head motion, side-to-side head motion, tilting head motion, body leaning motion, gaze direction, and so on. The mental state data can be captured using a camera, an accelerometer, eye-tracking glasses, or other types of sensors. In some embodiments, the collecting of mental state data can be accomplished with a mobile device, a handheld device, a personal electronic device, etc. The flow 100 includes performing face detection 114 to determine when the individual is looking in a direction of one or more cameras. Any camera or image capture device suitable for data collection can be used. In embodiments, the flow 100 includes identifying a second face 118 from a second individual within the series of images. The second face can appear in a given image with the first face, can appear alone in an image, and so on. The flow 100 can include filtering out faces 116 of one or more other people in an image to determine when the first individual is looking in the direction of a camera. The detection of a given face can be based on image classifiers. The image classifiers can be algorithms, pieces of code, heuristics, etc., that can be used to detect a face in one or more images.

The flow 100 includes using one or more processors for obtaining analysis 130 of the mental state data on the individual. The one or more processors can be located locally or remotely. For example, the processors for obtaining analysis can be collocated with image capture, included in a user device, and so on. The flow 100 can further include analyzing 132 the mental state data to produce mental state information. In some embodiments, the analysis 132 of the mental state data can be performed locally, such as on the computer that is coupled to the sensors collecting the mental state data from the individual, or on the computer, mobile device, handheld device, etc., with which the individual is interacting. The flow 100 can further include sending 134 one or more of the mental state data, a subset of the mental state data, or an initial analysis of the mental state data to a web service for further analysis, storage, or other purposes. The sending 134 can be accomplished on a periodic basis or an occasional basis, and can be sent using a different time basis than the one used in the data collection. For example, the mental state data can be collected on an opportunistic or random intermittent basis, and the mental state data can be sent on either a periodic or occasional basis. The flow 100 can further include sending a request 136 to a web service for the analysis or data processing activities related to the mental state data. The web service can generate the analysis 138 of the mental state data. The web service that can generate the analysis can include cloud computation. The flow 100 can include obtaining analysis 150 of the mental state data on the individual. This obtaining analysis 150 can include diverse methods, including, but not limited to, analyzing the mental state data locally, analyzing the mental state data remotely, receiving an analysis of the mental state data directly from a smart sensor, generating the analysis on a co-processor or dedicated subsystem, and so on. The obtaining analysis 150 of the mental state data can be based on sending a request to a web service 152 for the analysis. The web service that can perform the analysis can be located on the data collection machine, located remotely, located on the Internet, and so on. In embodiments, the analysis of the mental state data can be performed locally on a computer, on a mobile device, on a handheld device, and so on. The analysis of the mental state data can be received from a web service. The web service could be located remotely, on a handheld device, on a laptop computer, and so on. The web service can include a subscription service, a cloud service, etc. The web service can provide analysis operations, can receive mental state data for analysis, and so on. The flow 100 includes sending one or more of the mental state data, a subset of the mental state data, or an initial analysis of the mental state data to the web service. Any amount of mental state data can be sent to the web service. The sending of mental state date can be accomplished on a periodic basis. Mental state data can be sent to the web service sporadically, intermittently, periodically, continuously, and so on.

The flow 100 includes interpolating 140 mental state data in between the collecting which is intermittent. Interpolating 140 can be performed using any suitable algorithm including piecewise constant interpolation, linear interpolation, polynomial interpolation, bicubic interpolation, a Gaussian process, one of the numerous and various curve fitting algorithms known in the art, or any other algorithm. In some embodiments, the interpolating 140 can be performed for mental state analysis in between the collecting which is intermittent. The flow 100 can include imputing 142 additional mental state data where the mental state data is missing. When the mental state data is collected 110 on an intermittent basis, there can be times when the mental state data is not collected and thus can be missing. This missing mental state data can be imputed, or predicted, based on other data. The imputation can be based on other data collected from the individual on whom the data is missing. In other cases, the imputation can be based on mental state data collected from other individuals around the individual on whom the data is missing. The other individuals can be geographically nearby or may be part of the individual's social network. Thus, the missing mental state data can be imputed based on mental state data for other people in the social network of the individual.

The flow 100 can further include inferring mental states 144 based on the mental state data which can be collected. Mental states that can be inferred can include one or more of a group including enjoyment, happiness, anger, sadness, stress, frustration, confusion, disappointment, hesitation, cognitive overload, focusing, being engaged, attending, boredom, exploration, confidence, trust, delight, and satisfaction. The flow 100 can further include determining contextual information 146 which can be based on sensor data or other types of data such as the application being used on the computer, the time of day, or any other type of contextual information. The contextual information can be based on one or more of skin temperature or accelerometer data. In embodiments, other physiological information can be included in contextual information, where the physiological data can include one or more of electrodermal activity, heart rate, heart rate variability, skin temperature, or respiration, and so on. The contextual information can be based on one or more of a photograph, an email, a text message, a phone log, or GPS information. The flow 100 further includes comparing the mental state data against a plurality of mental state event temporal signatures 148.

The flow 100 includes rendering an output based on the analysis of the mental state data where the rendering includes output usage 160. An output can be rendered 162 based on the mental state data and/or the mental state. Depending on the embodiment, the output can include text, icons, pictures, graphs, binary data, or any other form or output that may be interpreted by a person or another computer. The rendered output can be used in various ways, including presenting the rendered output to the individual, storing the rendered output, sending the rendered output to a central collection point, printing the rendered output, etc. The flow 100 further includes posting the analysis 164 to a social network page. The posting to the social network page can be the rendered output or can be at least a portion of the mental state data or information regarding the mental state.

The flow 100 includes tracking a face 170 for the individual within the series of images. The tracking of the face can include scaling, rotation, translation, etc. of the face. The tracking can include the face leaving from a subsequent image in a series of images. The tracking can include the face reappearing in a subsequent image in a series of images, etc. The flow 100 includes tracking the second face 172 within the series of images. As with the first face, the tracking of the second face can include scaling, rotation, translation, leaving, reappearing, and so on. Other facial tracking techniques can include performing face detection to determine when the individual is looking in the direction of the camera. The flow 100 further includes filtering out faces of one or more other people to determine when the individual is looking in the direction of a camera. If an image includes more than one face, then faces other than the one from which facial data is being collected can be filtered out to improve the data collection from the single face of interest. In embodiments, facial data can be collected from an individual when the individual is looking in the direction of one of more cameras. The timing of the collection of the data, the type of data collected, and so on can be determined by the type of camera being looked at by the individual, the time at which the individual is looking, what tasks the individual is performing at the time of the looking, and so on. The flow 100 further includes translating the mental state data into an emoji 174 for representation of the individual. An emoji, pictograph, emoticon, etc., can represent facial expressions, places, animals, food, cultural items, and so on. An emoji can be shared by the individual with others including friends, family, and so on, through social media, email messages, text (SMS) messages, and so on. The emoji can be automatically selected based on the mental state data, chosen by the individual, chosen by others to represent one or more mental states of the individual, and so on.

The flow 100 includes inferring mental states 144 based on the mental state data which was collected. The mental state or states that can be inferred can be based on analyzing the facial data using classifiers. As mentioned above, the one or more classifiers can be algorithms, heuristics, pieces of code, and so on. The classifiers can be based on facial action units from the facial action coding system (FACS). The inferring can include detection of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, poignancy, or mirth. Any human mood, emotion, etc., can be inferred from the analysis based on the classifiers. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors. Various embodiments of the flow 100, or portions thereof, can be included on a semiconductor chip and implemented in special purpose logic, programmable logic, and so on.

Figure 2:
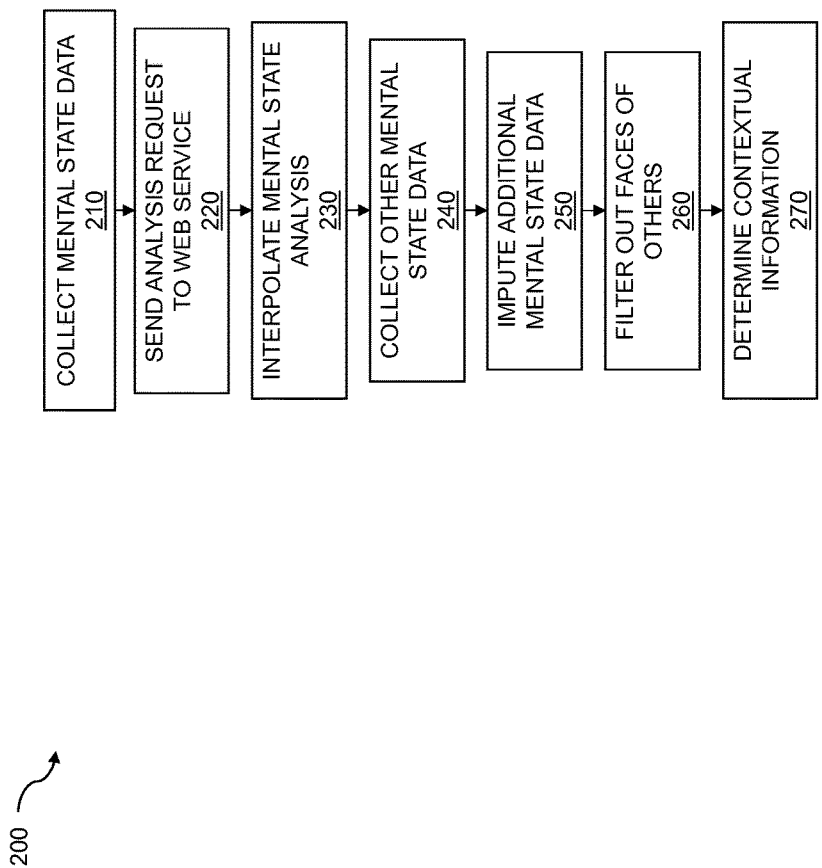
FIG. 2 is a flow diagram for web-based analysis of mental states.

FIG. 2 is a flow diagram for web-based analysis of mental states. The flow 200 includes collecting mental state data 210 from an individual on an intermittent basis. In embodiments, the mental state data can be collected periodically, continuously, and so on. The mental state data that can be collected can include facial data, physiological data, accelerometer data, and so on. The physiological data can include one or more of electrodermal activity, heart rate, heart rate variability, skin temperature, respiration, and other physiological factors. The flow 200 includes sending a request to a web service 220 for the analysis where the analysis of the mental state data is received from a web service. The request that is sent to the web service can include collection of mental state data, analysis of mental state data, rendering of mental state data, inferring of mental states, selection of one or more emoji, and so on. The flow 200 includes interpolating mental state analysis 230 in between the collecting which is intermittent. Since the collection of mental state data can be intermittent, sporadic, periodic, and so on, there can be gaps in the data when no mental state data or insufficient mental state data can be collected. The interpolation can be used to compute mental state data between the collections of mental state data. The flow 200 includes collecting other mental state data 240, including electrodermal activity data, from the individual on a continuous basis. The other mental state data can be collected on an intermittent, sporadic, or periodic basis. The other mental state data can include other physiological data, accelerometer data, and so on. The flow 200 includes imputing additional mental state data 250 where the mental state data is missing. The data can be missing because of the intermittent collection of the data, because the individual is not facing a camera so no data is being collected, and so on. The flow 200 includes filtering out faces 260 of one or more other people to determine when an individual is looking in a direction of a camera. An image can contain a plurality of people and a plurality of faces. When more than one face is visible in an image, the faces other than the face of the individual can be filtered out. The remaining face, that of the individual, can then be examined to determine whether the individual is facing one or more cameras, and, if so, facial data can be collected using the one or more cameras. The flow 200 includes determining contextual information 270 based on accelerometer data. The contextual information can be based any number of parameters and can include time, GPS coordinates, physiological parameters including skin temperature, accelerometer data, and so on. The contextual data can be used in the analysis of the mental state data to infer mental states, moods, and so on of the individual. The contextual information can be used in the inferring where the inferring includes detection of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, poignancy, mirth, and so on. The contextual information can be based on one or more of a photograph, an email, a text message, a phone log, GPS information, etc. Various steps in the flow 200 may be changed in order, repeated, omitted, or the like without departing from the disclosed concepts. Various embodiments of the flow 200 may be included in a computer program product embodied in a non-transitory computer readable medium that includes code executable by one or more processors. Various embodiments of the flow 200, or portions thereof, can be included on a semiconductor chip and implemented in special purpose logic, programmable logic, and so on.

Figure 3:
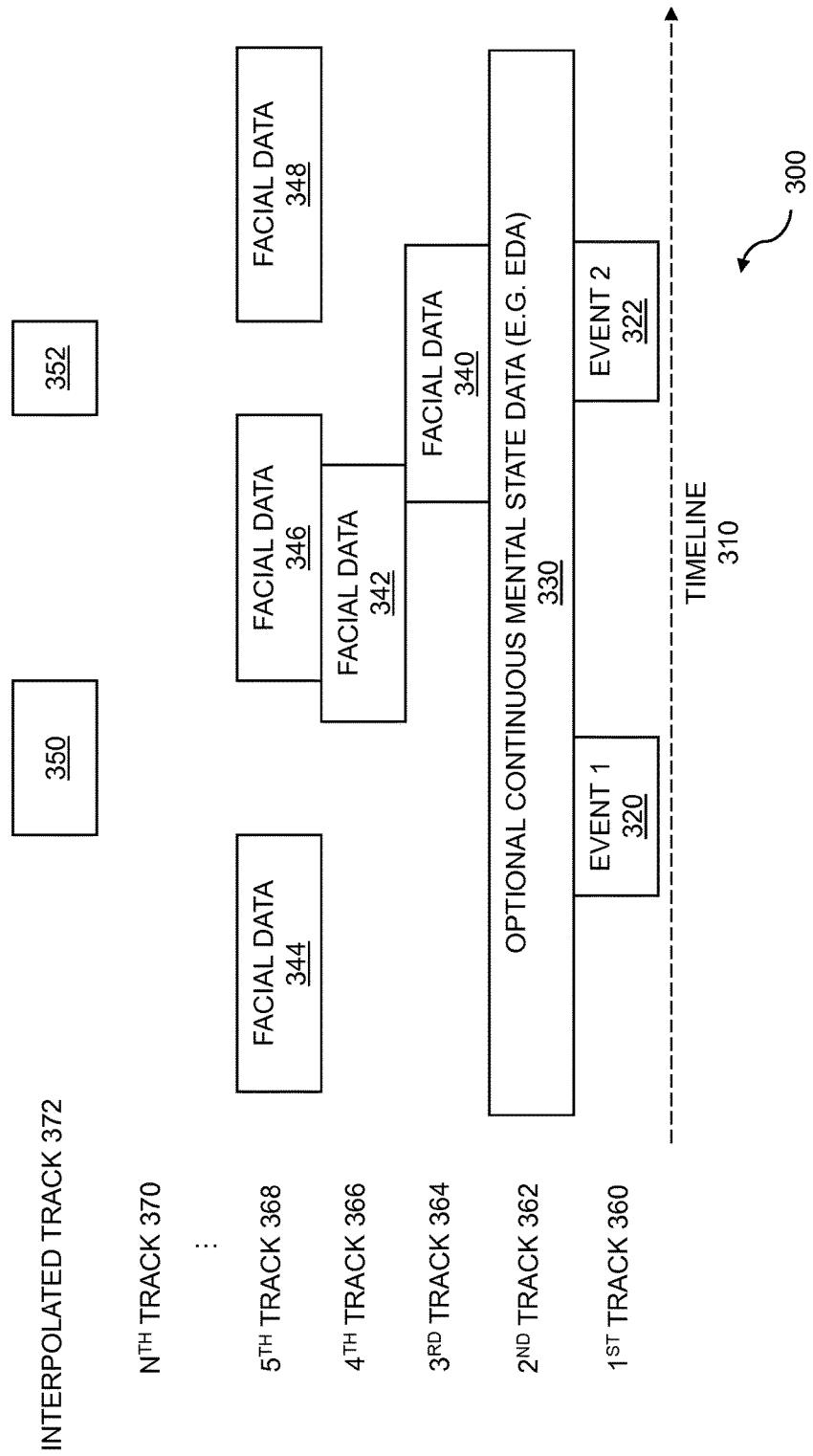
FIG. 3 is a timeline with information tracks relating to mental states.

FIG. 3 is a timeline with information tracks relating to mental states. A timeline 310 can show information tracks 300, where the information that can be represented by the tracks can be collected on an intermittent basis. A first track 360 shows events that may be related to the individual's use of a computer or other device. A first event 320 may indicate an action that the individual took (such as launching an application); an action initiated by the computer (such as the presentation of a dialog box); an external event (such as a new global positioning system (GPS) coordinate); or receiving an e-mail message, a phone call, a text message, or any other type of event. In some embodiments, a photograph may be used to document an event or simply save contextual information in the first track 360. A second event 322 may indicate another action or event. Such events can be used to provide contextual information and can also include such things as copies of email messages, text messages, phone logs, file names, or other information that may be useful to understanding the context of a user's actions. In embodiments, contextual information can be based on one or more of a photograph, an email, a text message, a phone log, or GPS information.

A second track 362 can include continuously collected mental state data such as electrodermal activity data 330. In embodiments, a track can include intermittently collected mental state data. The intermittently collected data can be collected when an individual is present in an image and not collected when the individual is absent from the image, for example. The intermittently collected data can include facial data where the facial data is collected intermittently when the individual can be looking in a direction of a camera. The camera can be a still camera, a video camera, a camera coupled to a mobile device, etc. The intermittent data collection can occur across multiple devices. For example, when the individual is facing a smartphone, then the facial data can be collected from the camera coupled to the smartphone; when the individual is facing a laptop, then the facial data can be collected from the camera coupled to the laptop, and so on. Any number of devices can be used to collect facial data intermittently over time.

A third track 364 can include facial data 340, which can be a type of mental state data that is collected on an intermittent basis by a first camera, such as the room camera (although in some embodiments, the facial data can be collected continuously). The facial data can be collected intermittently when the individual is looking toward a camera. The facial data 340 can include one or more still photographs, videos, or abstracted facial expressions which can be collected when the user looks in the direction of the camera. A fourth track 366 can include facial data 342 that can be collected on an intermittent or continuous basis by a second camera, such as the mobile phone camera. The facial data 342 can include one or more still photographs, videos, or abstracted facial expressions which can be collected when the user looks in the direction of that camera. A fifth track 368 can include facial data that is collected from a third camera, such as the webcam. In the example shown, the fifth track 368 includes facial data 344, facial data 346, and facial data 348 which can be any type of facial data including data that can be used for determining mental state information. Any number of samples of facial data can be collected in any track. The mental state data from the various tracks can be collected simultaneously, collected on one track exclusive of other tracks, collected where mental state data overlaps between the tracks, and so on. When mental state data from multiple tracks overlaps, one track's data can take precedence or the data from the multiple tracks can be combined.

Additional tracks, through the $n^{th}$ track 370, of mental state data of any type may be collected. The additional tracks 370 can be collected on a continuous or on an intermittent basis. The tracks can include mental state data including audio voice data. The mental state data of an individual can include audio voice data on an intermittent basis. The intermittent basis for mental state data can be either occasional or periodic. The intermittent basis can occur when the individual is facing a camera. The analysis can further include interpolating mental state analysis in between the collecting which is intermittent; collecting other mental state data, including electrodermal activity data, from the individual on a continuous basis; imputing additional mental state data where the mental state data is missing; filtering out faces of one or more other people to determine when an individual is looking in a direction of a camera; determining contextual information based on accelerometer data; and sending a request to a web service for the analysis where the analysis of the mental state data is received from a web service. The intermittent collection of mental state data can include multiple devices where the data collection can take place when the individual is looking in the direction of at least one of the plurality of image collection devices.

One or more interpolated tracks 372 may be included and may be associated with mental state data that is collected on an intermittent basis, such as the facial data of the fifth track 368. Interpolated data 350 and interpolated data 352 may contain interpolations of the facial data of the fifth track 368 for the time periods where no facial data was collected in that track. Other embodiments interpolate data for periods where no track includes facial data. In other embodiments, analysis includes interpolating mental state analysis when the mental state data collected is intermittent.

The mental state data, such as the continuous mental state data 330 and/or any of the collected facial data 340, 342, 344, 346, and 348 can be tagged. The tags can include metadata related to the mental state data, including, but not limited to, the device that collected the mental state data; the individual from whom the mental state data was collected; the task being performed by the individual; the media being viewed by the individual; and the location, environmental conditions, time, date, or any other contextual information. The tags can be used to locate pertinent mental state data; for example, the tags may be used to retrieve the mental state data from a database. The tags can be included with the mental state data that is sent over the internet to cloud or web-based storage and/or services so that the tags may be used locally on the machine where the mental state data was collected and/or remotely on a remote server or a cloud/web service.

Figure 4:
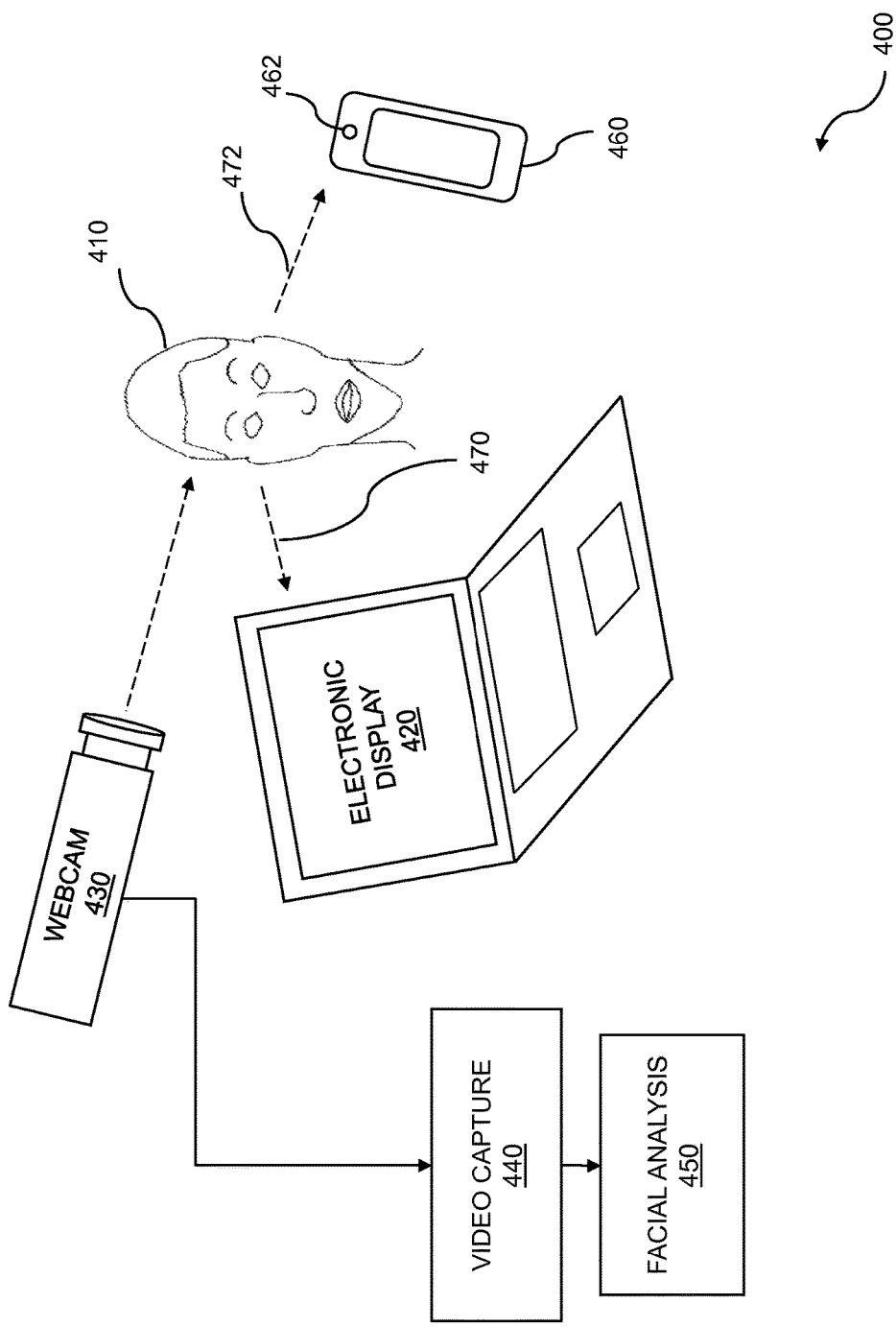
FIG. 4 is a diagram for facial analysis.

FIG. 4 is a diagram for facial analysis 400. An individual 410 may view 470 an electronic display 420 while mental state data on the individual 410 may be collected and analyzed. The mental state data can be collected sporadically with mobile affect data. The electronic display 420 may show an output of a computer application that the individual 410 is using, or the electronic display 420 may show a media presentation in a manner which exposes the individual 410 to the media presentation. The media presentation may include one of a group consisting of a movie, a television show, a web series, a webisode, a video, a video clip, an electronic game, an e-book, or an e-magazine. The electronic display 420 may be a part of, or may be driven from, the device collecting the mental state data or, depending on the embodiment, the electronic display may only be loosely coupled to, or may be unrelated to, the device collecting the mental state data. The collecting, in some embodiments, is accomplished with a mobile device 460, such as a cell phone, a tablet computer, or a laptop computer, and the mobile device may include a forward facing camera 462 when the user views 472 the mobile device 460. The facial data may be collected with a camera such as the forward facing camera 462 of the mobile device 460 and/or by a webcam 430. The facial data may be collected intermittently when the individual 410 is looking in the direction of a camera 462 or 430. The camera may also capture images of the setting. These images may be used in determining contextual information.

The webcam 430 may be used to collect one or more of facial data and physiological data. The facial data may include, in various embodiments, information on facial expressions, action units, head gestures, smiles, smirks, brow furrows, squints, lowered eyebrows, raised eyebrows, or attentiveness. The webcam 430 may capture video, audio, and/or still images of the individual 410. A webcam, as the term is used herein, may include a video camera, still camera, thermal imager, CCD device, phone camera, three-dimensional camera, a depth camera, multiple webcams used to show different views of a person, or any other type of image capture apparatus that may allow data captured to be used in an electronic system. The images of the person 410 from the webcam 430 may be captured by a video capture unit 440. In some embodiments, video may be captured, while in others, one or more still images may be captured. The captured video or still images may be used in facial analysis 450 or for determining gestures, actions, or other movements.

Analysis of facial expressions, gestures, and mental states may be accomplished using the captured images of the person 410. The facial expressions may be used to identify smiles, frowns, and other facial indicators of mental states. The gestures, including head gestures, may indicate interest or curiosity. For example, a head gesture of moving toward the electronic display 420 may indicate increased interest in the media or desire for clarification. Based on the captured images, analysis of physiological data may be performed. Respiration, heart rate, heart rate variability, perspiration, temperature, and other physiological indicators of mental state may be determined by analyzing the images.

Figure 5:
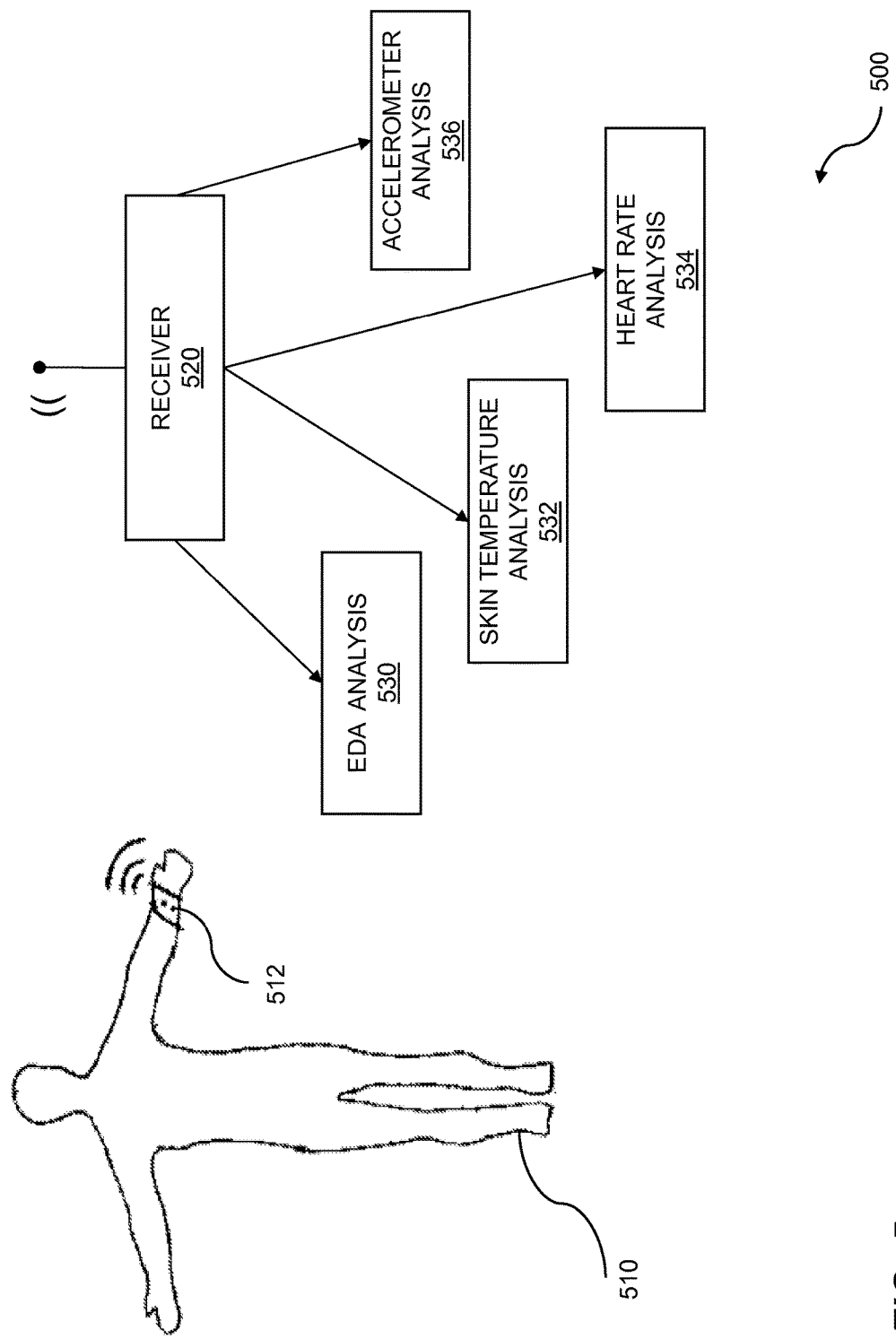
FIG. 5 is diagram for sensor analysis.

FIG. 5 is diagram for sensor analysis. A system 500 may analyze data collected intermittently from a person 510 as he or she interacts with a computer, a mobile device, a handheld device, and so on. The person 510 may have a biosensor 512 attached to him or her for the purpose of collecting mental state data. The biosensor 512 may be placed on the wrist, palm, hand, head, or other part of the body. In some embodiments, multiple biosensors may be placed on the body in multiple locations. The biosensor 512 may include detectors for physiological data such as electrodermal activity, skin temperature, accelerometer readings, and the like. Other detectors for physiological data may be included as well, such as heart rate, blood pressure, EKG, EEG, further brain waves, and other physiological detectors. The biosensor 512 may transmit information collected to a receiver 520 using wireless technology such as Wi-Fi, Bluetooth, 802.11, cellular, or other bands. In other embodiments, the biosensor 512 may communicate with the receiver 520 by other methods such as a wired interface or an optical interface. The receiver may provide the data to one or more components in the system 500. In some embodiments, the biosensor 512 may record multiple types of physiological information in memory for later download and analysis. In some embodiments, the download of recorded physiological data may be accomplished through a USB port or other wired or wireless connection.

Mental states may be inferred based on physiological data, such as physiological data from the sensor 512. Mental states may also be inferred based on facial expressions and head gestures observed by a webcam, or a combination of data from the webcam and data from the sensor 512. The mental states may be analyzed based on arousal and valence. Arousal can range from being highly activated—such as when someone is agitated—to being entirely passive—such as when someone is bored. Valence can range from being very positive—such as when someone is happy—to being very negative—such as when someone is angry. Physiological data may include one or more of electrodermal activity (EDA), heart rate, heart rate variability, skin temperature, respiration, accelerometer readings, and other types of analysis of a human being. It will be understood that both here and elsewhere in this document, physiological information can be obtained either by biosensor 512 or by facial observation via the webcam 530. Facial data may include facial actions and head gestures used to infer mental states. Further, the data may include information on hand gestures or body language and body movements such as visible fidgets. In some embodiments, these movements may be captured by cameras, while in other embodiments, these movements may be captured by sensor readings. Facial data may include the tilting the head to the side, leaning forward, smiling, frowning, and many other gestures or expressions.

Electrodermal activity may be collected in some embodiments. It may be collected continuously, every second, four times per second, eight times per second, 32 times per second, or on some other periodic basis. In some embodiments, however, electrodermal activity may be collected on an intermittent basis. The electrodermal activity may be recorded and stored onto a disk, a tape, flash memory, a computer system, or streamed to a server. The electrodermal activity may be analyzed 530 to indicate arousal, excitement, boredom, or other mental states based on observed changes in skin conductance. Skin temperature may be collected and/or recorded on a periodic basis. In turn, the skin temperature may be analyzed 532. Changes in skin temperature may indicate arousal, excitement, boredom, or other mental states. Heart rate may be collected and recorded, and may also be analyzed 534. A high heart rate may indicate excitement, arousal, or other mental states. Accelerometer data may be collected and used to track one, two, or three dimensions of motion. The accelerometer data may be recorded. The accelerometer data may be used to create an actigraph showing an individual's activity level over time. The accelerometer data may be analyzed 536 and may indicate a sleep pattern, a state of high activity, a state of lethargy, or other states. The various data collected by the biosensor 512 may be used along with the facial data captured by the webcam in the analysis of mental states. Contextual information may be based on one or more of skin temperature and/or accelerometer data.

Figure 6:
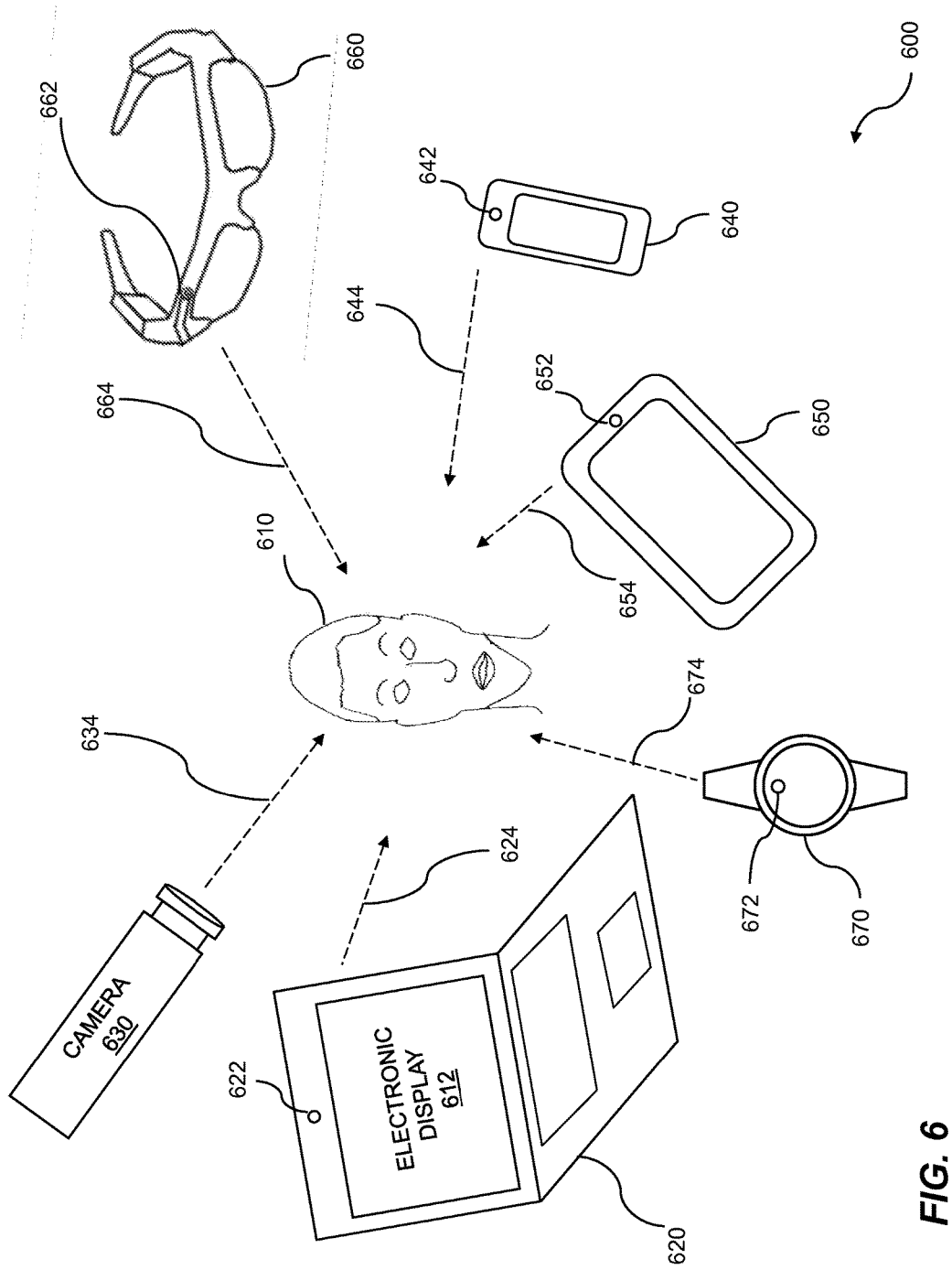
FIG. 6 is a diagram showing mental state data, including facial data, collection from multiple devices.

FIG. 6 is a diagram showing mental state data, including facial data, collection from multiple devices. The collection of mental state data from multiple machines can be sporadic, where the collection can take place when a person is looking in the direction of a camera, for example. The multiple mobile devices 600 can be used singly or together to collect video data on a person 610 and can be used with mobile affect data and in the translation of facial expressions into emoji. While one person is shown, in practice, the video data on any number of people can be collected. A user 610 can be observed as she or he is performing a task, experiencing an event, viewing a media presentation, and so on. The user 610 can be shown one or more media presentations, political presentations, or social media, for example, or another form of displayed media. The one or more media presentations can be shown to a plurality of people. The media presentations, for example, can be displayed on an electronic display 612 or another display. The data collected on the user 610 or on a plurality of users can be in the form of one or more videos, video frames, still images, etc. The plurality of videos can be of people who are experiencing different situations. Some example situations can include the user or plurality of users being exposed to TV programs, movies, video clips, social media, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 610 can be analyzed and viewed for a variety of purposes including expression analysis, mental state analysis, and so on. The electronic display 612 can be on a laptop computer 620 as shown, a tablet computer 650, a cell phone 640, a television, a mobile monitor, or any other type of electronic device. In an embodiment, expression data is collected on a mobile device such as a cell phone 640, a tablet computer 650, a laptop computer 620, or a watch 670. Thus, the multiple sources can include at least one mobile device, such as a phone 640 or a tablet 650, or a wearable device such as a watch 670 or glasses 660. A mobile device can include a forward facing camera and/or a rear-facing camera that can be used to collect expression data. Sources of expression data can include a webcam 622, a phone camera 642, a tablet camera 652, a wearable camera 662, and a mobile camera 630. A wearable camera can comprise various camera devices such as the watch camera 672.

As the user 610 is monitored, the user 610 may move due to the nature of the task, boredom, discomfort, distractions, or for another reason. As the user moves, the camera that has a view of the user's face can be changed. Thus, as an example, if the user 610 is looking in a first direction, the line of sight 624 from the webcam 622 is able to observe the individual's face but if the user is looking in a second direction, the line of sight 634 from the mobile camera 630 is able to observe the individual's face. Further, in other embodiments, if the user is looking in a third direction, the line of sight 644 from the phone camera 642 is able to observe the individual's face, and if the user is looking in a fourth direction, the line of sight 654 from the tablet camera 652 is able to observe the individual's face. If the user is looking in a fifth direction, the line of sight 664 from the wearable camera 662, which can be a device such as the glasses 660 shown and can be worn by another user or an observer, is able to observe the individual's face. If the user is looking in a sixth direction, the line of sight 674 from the wearable watch-type device 670 with a camera 672 included on the device is able to observe the individual's face. In other embodiments, the wearable device is a another device, such as an earpiece with a camera, a helmet or hat with a camera, a clip-on camera attached to clothing, or any other type of wearable device with a camera or another sensor for collecting expression data. The individual 610 can also use a wearable device including a camera for gathering contextual information and/or collecting expression data on other users. Because the individual 610 can move her or his head, the facial data can be collected intermittently when the individual is looking in a direction of a camera. In some cases, multiple people are included in the view from one or more cameras, and some embodiments include filtering out faces of one or more other people to determine whether the individual 610 is looking toward a camera. All or some of the expression data can be continuously or sporadically available from these various devices and other devices.

The captured video data can include facial expressions and can be analyzed on a computing device such as the video capture device or on another separate device. For example, the analysis could take place on one of the mobile devices discussed above, on a local server, on a remote server, and so on. In embodiments, some of the analysis can take place on the mobile device while other analysis can take place on a server device. The analysis of the video data can include the use of a classifier. For example, the video data can be captured using one of the mobile devices discussed above and sent to a server or another computing device for analysis. However, the captured video data including expressions can also be analyzed on the device which performed the capturing. For example, the analysis can be performed on a mobile device where the videos were obtained with the mobile device and wherein the mobile device includes one or more of a laptop computer, a tablet, a PDA, a smartphone, a wearable device, and so on. In another embodiment, the analyzing can comprise using a classifier on a server or other computing device other than the capturing device.

Figure 7:
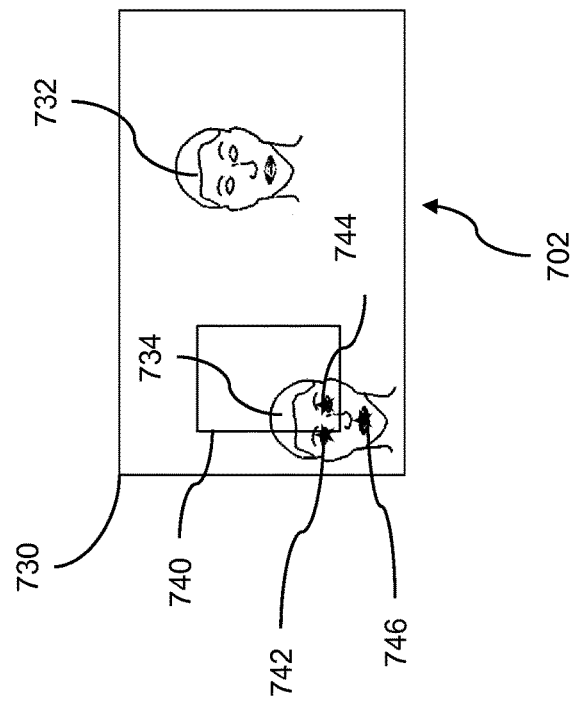
FIG. 7 illustrates feature extraction for multiple faces.
Figure 7:
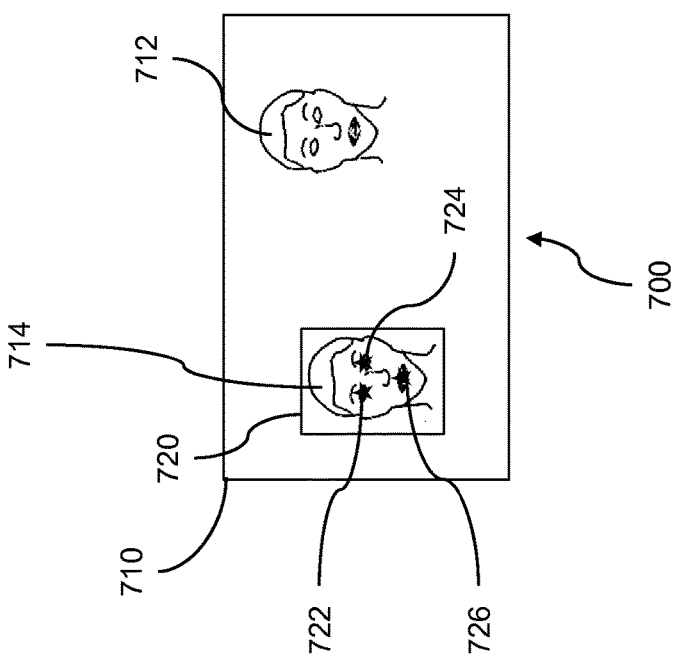

FIG. 7 illustrates feature extraction for multiple faces. Features of a face or a plurality of faces can be extracted from sporadically collected video data and can be used with mobile affect data. The mobile affect data can be translated to emoji representing facial expressions. The feature extraction can be performed by analysis using one or more processors, using one or more a video collection devices, and by using a server, for example. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code, for example, by analyzing a known set of data, known as a training set. The training set can include data for which category memberships of the data can be known. The training set can be used as part of a supervised training technique. If a training set is not available, then a clustering technique can be used to group observations into categories. This latter approach, or unsupervised learning, can be based on a measure (i.e. distance) of one or more inherent similarities among the data that is being categorized. When the new observation is received, then the classifier can be used to categorize the new observation. Classifiers can be used for many analysis applications including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. For example, classification of one or more observations into one or more groups can be based on distributions of the data values, probabilities, and so on. Classifiers can be binary, multiclass, linear and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on.

Classification can be used for biometric identification of one or more people in one or more frames of one or more videos.

Returning to FIG. 7, the detection of the first face, the second face, and so on for any number of faces can include identifying facial landmarks, generating a bounding box, and prediction of a bounding box and landmarks for a next frame, where the next frame can be one of a plurality of frames of a video containing faces. In some embodiments, landmark analysis is avoided and instead regions of a face are analyzed. A first video frame 700 includes a boundary 710, a first face 712, and a second face 714. The frame 700 also includes a bounding box 720. Facial landmarks can be generated for the first face 712. Face detection can be performed to initialize a second set of locations for a second set of facial landmarks for a second face within the video. Facial landmarks in the video frame 700 can include the facial landmarks 722, 724, and 726. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. For example, the estimating of a second rough bounding box can include the bounding box 720. Bounding boxes can also be estimated for one or more other faces within the frame 710. The bounding box can be refined, as can one or more facial landmarks. The refining of the second set of locations for the second set of facial landmarks can be based on localized information around the second set of facial landmarks. The bounding box 720 and the facial landmarks 722, 724, and 726 can be used to estimate future locations for the second set of locations for the second set of facial landmarks in a future video frame from the first video frame.

A second video frame 702 is also shown. The second video frame 702 includes a frame boundary 730, a first face 732, and a second face 734. The second frame 702 also includes a bounding box 740 and the facial landmarks 742, 744, and 746. In other embodiments, any number of facial landmarks are generated and used for facial tracking of the two or more faces of a video frame, such as the shown second video frame 702. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, any number of facial points can be determined within a frame. One or more of the other facial points that are determined can correspond to a third face. The location of the bounding box 740 can be estimated, where the estimating can be based on the location of the generated bounding box 720 shown in the prior frame 700. The three facial points shown, facial points 742, 744, and 746, might lie within the bounding box 740 or might not lie partially or completely within the bounding box 740. For example, the second face 734 might have moved between the first video frame 700 and the second video frame 702. Based on the accuracy of the estimating of the bounding box 740, a new estimation can be determined for a third, future frame from the video, and so on. The evaluation can be performed, all or in part, on semiconductor based logic.

Figure 8:
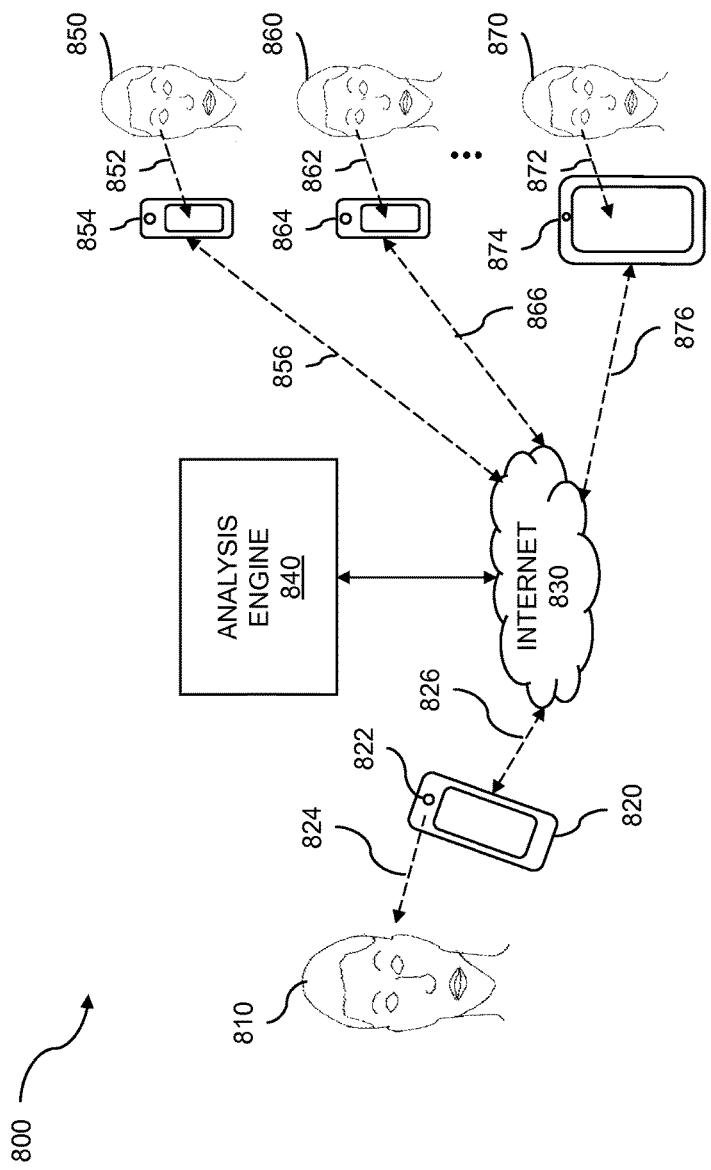
FIG. 8 shows live streaming of social video.

FIG. 8 shows live streaming of social video. Features of a face or a plurality of faces can be extracted from sporadically collected video data and can be used with mobile affect data. The sporadically collected video and associated mental state analysis can be transmitted in a live-stream fashion. Interpolated mental state analysis can be transmitted as part of the live-stream information. The mobile affect data can be streamed as video or translated to emoji representing facial expressions. The streaming and analysis can be facilitated by a video capture device, a local server, a remote server, a semiconductor based logic, and so on. The streaming can be live-streaming. Such streaming can include mental state analysis, mental state event signature analysis, etc. Live-streaming video is an example of one-to-many social media, where video can be sent over the Internet from one person to a plurality of people using a social media app and/or platform. Live-streaming is one of numerous popular techniques used by people who want to disseminate ideas, send information, provide entertainment, share experiences, and so on. Some of the live-streams can be scheduled, such as webcasts, online classes, sporting events, news, computer gaming, or videoconferences, while others can be impromptu streams that are broadcast as needed or when desirable. Examples of impromptu live-stream videos can range from individuals simply wanting to share experiences with their social media followers, to live coverage of breaking news, emergencies, or natural disasters. The latter coverage can be known as mobile journalism, or "mo jo", and is becoming increasingly common. With this type of coverage, "reporters" can use networked, portable electronic devices to provide mobile journalism content to a plurality of social media followers. Such reporters can be quickly and inexpensively deployed as the need or desire arises.

Several live-streaming social media apps and platforms can be used for transmitting video. One such video social media app is Meerkat™ that can link with a user's Twitter™ account. Meerkat™ enables a user to stream video using a handheld, networked electronic device coupled to video capabilities. Viewers of the live-stream can comment on the stream using tweets that can be seen by and responded to by the broadcaster. Another popular app is Periscope™ that can transmit a live recording from one user to that user's Periscope™ account and other followers. The Periscope™ app can be executed on a mobile device. The user's Periscope™ followers can receive an alert whenever that user begins a video transmission. Another live-stream video platform is Twitch™ that can be used for video streaming of video gaming and broadcasts of various competitions and events.

The example 800 shows a user 810 broadcasting a video live-stream to one or more people 850, 860, 870, and so on. A portable, network-enabled electronic device 820 can be coupled to a forward-facing camera 822. The portable electronic device 820 can be a smartphone, a PDA, a tablet, a laptop computer, and so on. The camera 822 coupled to the device 820 can have a line-of-sight view 824 to the user 810 and can capture video of the user 810. The captured video can be sent to an analysis or recommendation engine 840 using a network link 826 to the Internet 830. The network link can be a wireless link, a wired link, and so on. The recommendation engine 840 can recommend to the user 810 an app and/or platform that can be supported by the server and can be used to provide a video live-stream to one or more followers of the user 810. In the example 800, the user 810 has three followers: the person 850, the person 860, and the person 870. Each follower has a line-of-sight view to a video screen on a portable, networked electronic device. In other embodiments, one or more followers follow the user 810 using any other networked electronic device, including a computer. In the example 800, the person 850 has a line-of-sight view 852 to the video screen of a device 854; the person 860 has a line-of-sight view 862 to the video screen of a device 864, and the person 870 has a line-of-sight view 872 to the video screen of a device 874. The portable electronic devices 854, 864, and 874 can each be a smartphone, a PDA, a tablet, and so on. Each portable device can receive the video stream being broadcasted by the user 810 through the Internet 830 using the app and/or platform that can be recommended by the recommendation engine 840. The device 854 can receive a video stream using the network link 856, the device 864 can receive a video stream using the network link 866, the device 874 can receive a video stream using the network link 876, and so on. The network link can be a wireless link, a wired link, a hybrid link, and so on. Depending on the app and/or platform that can be recommended by the recommendation engine 840, one or more followers, such as the followers 850, 860, 870, and so on, can reply to, comment on, and otherwise provide feedback to the user 810 using their devices 854, 864, and 874, respectively.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework.

The web-based framework can be used to display the video media presentation or event as well as to collect videos from any number of viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include such items as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. For example, the AUs can be used to recognize emotions experienced by the observed person. Emotion-related facial actions can be identified using the emotional facial action coding system (EM-FACS) and the facial action coding system affect interpretation dictionary (FACSAID), for example. For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, as well as specific emotions, moods, or mental states.

The coding of faces identified in videos captured of people observing an event can be automated. The automated systems can detect facial AUs or discrete emotional states.

The emotional states can include amusement, fear, anger, disgust, surprise, and sadness, for example. The automated systems can be based on a probability estimate from one or more classifiers, where the probabilities can correlate with an intensity of an AU or an expression. The classifiers can be used to identify into which of a set of categories a given observation can be placed. For example, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. For example, the image can be adjusted by flipping the image around a vertical line through the middle of a face in the image. The symmetry plane of the image can be determined from the tracker points and landmarks of the image.

In an embodiment, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions, and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor based logic.

Figure 9:
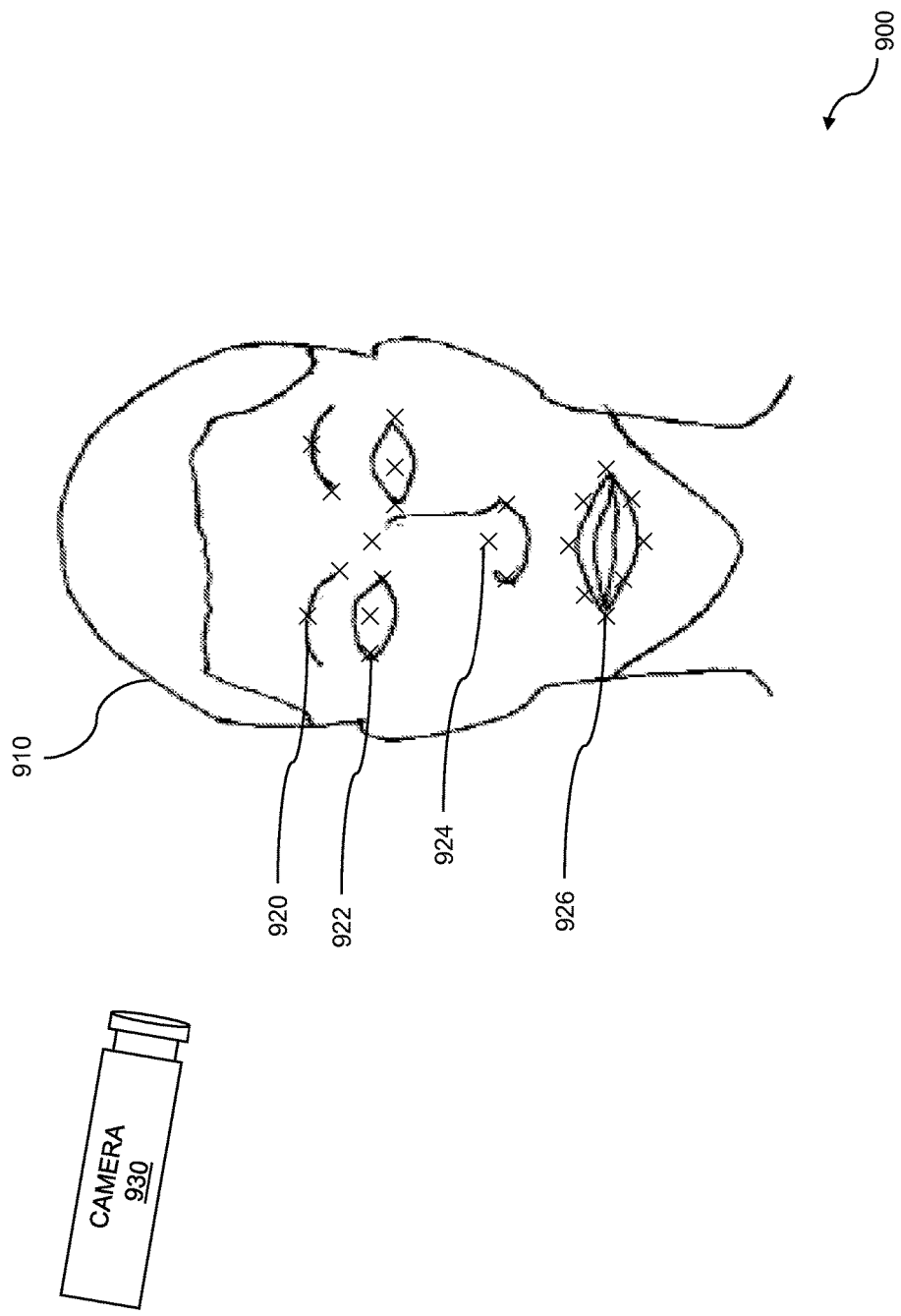
FIG. 9 shows example facial data collection including landmarks.

FIG. 9 shows example facial data collection including landmarks. Features of a face or a plurality of faces can be extracted from sporadically collected video data and can be used with mobile affect data. The mobile affect data can be translated to emoji representing facial expressions. Facial data including facial landmarks can be collected 900 using a variety of electronic hardware and software techniques. A face 910 can be observed using a camera 930 in order to collect facial data that includes facial landmarks. The facial data can be collected from a plurality of people using one or more of a variety of cameras. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend, for example, on the position of the camera 930 relative to the face 910, the number of cameras used, the illumination of the face, etc. For example, if the face 910 is poorly lit or over-exposed (e.g. in an area of bright light), the processing of the facial data to identify facial landmarks might be rendered more difficult. In another example, the camera 930 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 920, an outer eye edge 922, a nose 924, a corner of a mouth 926, and so on. Any number of facial landmarks can be identified from the facial data that is captured. The facial landmarks that are identified can be analyzed to identify facial action units. For example, the action units that can be identified can include AU02 outer brow raiser, AU14 dimpler, AU17 chin raiser, and so on. Any number of action units can be identified. The action units can be used alone and/or in combination to infer one or more mental states and emotions. A similar process can be applied to gesture analysis (e.g. hand gestures) with all of the analysis being accomplished or augmented by a mobile device, a server, semiconductor-based logic, and so on.

Figure 10:
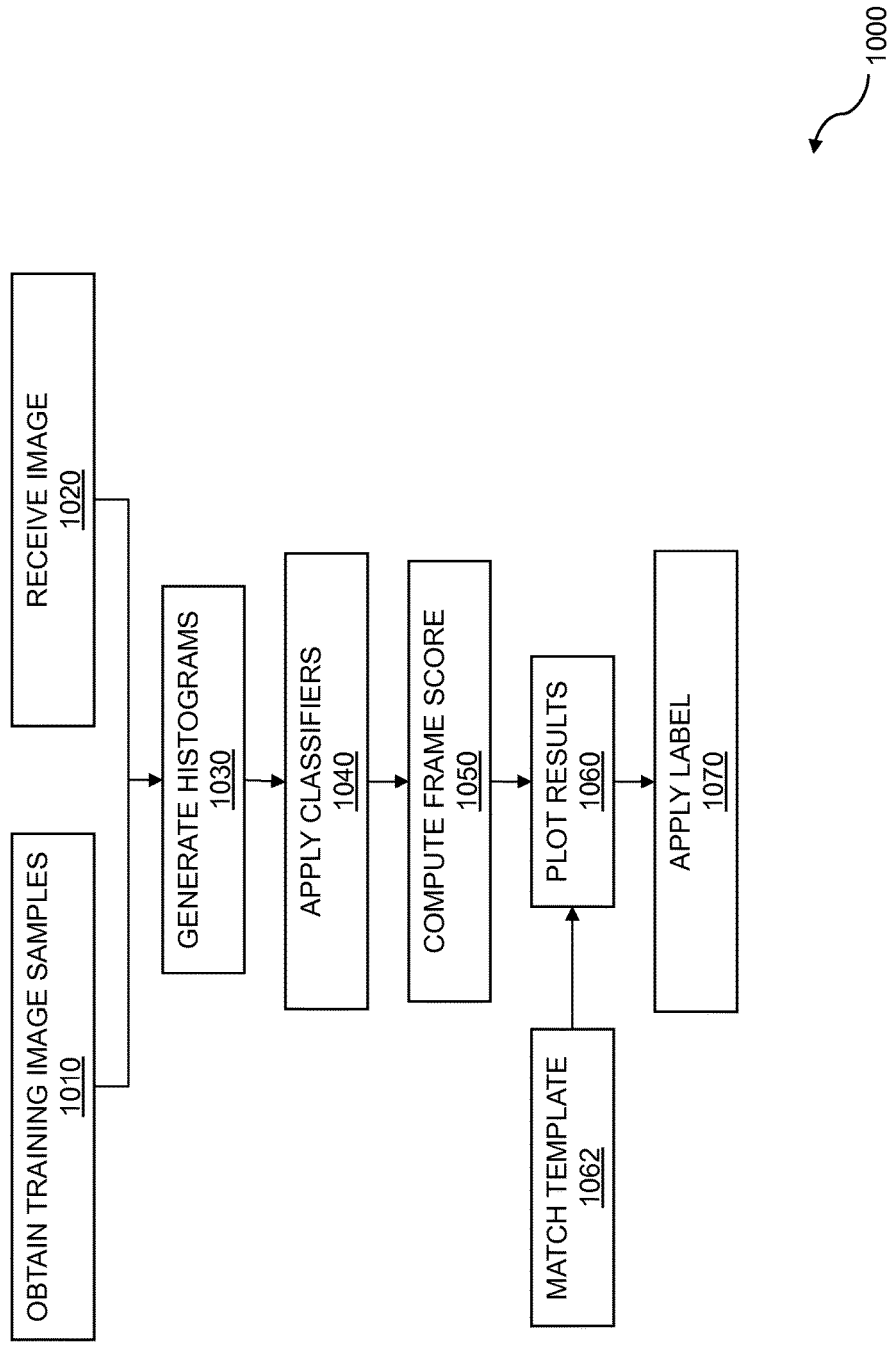
FIG. 10 is a flow diagram for detecting facial expressions.

FIG. 10 is a flow diagram for detecting facial expressions. Features of a face or a plurality of faces can be extracted from sporadically collected video data and can be used with mobile affect data. The mobile affect data can be translated to emoji representing facial expressions. The flow 1000, or portions thereof, can be implemented in semiconductor logic, can be accomplished using a mobile device, using a server device, and so on. The flow 1000 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU) where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1000 begins by obtaining training image samples 1010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, such as the camera 930 from FIG. 9, for example. The flow 1000 continues with receiving an image 1020. The image 1020 can be received from the camera 930. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system.

The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. For example, the manipulated image and a flipped or mirrored version of the manipulated image can be analyzed alone and/or in combination to improve analysis. The flow 1000 continues with generating histograms 1030 for the training images and the one or more versions of the received image. The histograms can be generated for one or more versions of the manipulated received image. The histograms can be based on a HoG or another histogram. As described above, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example.

The flow 1000 continues with applying classifiers 1040 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. For example, the classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1000 continues with computing a frame score 1050. The score computed for an image, where the image can be a frame from a video, can be used to determine the presence of a facial expression in the image or video frame. The score can be based on one or more versions of the image 1020 or a manipulated image. For example, the score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1000 continues with plotting results 1060. The results that are plotted can include one or more scores for one or more frames computed over a given time t. For example, the plotted results can include classifier probability results from analysis of HoGs for a sequence of images and video frames. The plotted results can be matched with a template 1062. The template can be temporal and can be represented by a centered box function or another function. A best fit with one or more templates can be found by computing a minimum error. Other best-fit techniques can include polynomial curve fitting, geometric curve fitting, and so on. The flow 1000 continues with applying a label 1070. The label can be used to indicate that a particular facial expression has been detected in the one or more images or video frames which constitute the image that was received 1020. For example, the label can be used to indicate that any of a range of facial expressions has been detected, including a smile, an asymmetric smile, a frown, and so on. Various steps in the flow 1000 may be changed in order, repeated, omitted, or the like without departing from the disclosed concepts. Various embodiments of the flow 1000 can be included in a computer program product embodied in a non-transitory computer readable medium that includes code executable by one or more processors. Various embodiments of the flow 1000, or portions thereof, can be included on a semiconductor chip and implemented in special purpose logic, programmable logic, and so on.

Figure 11:
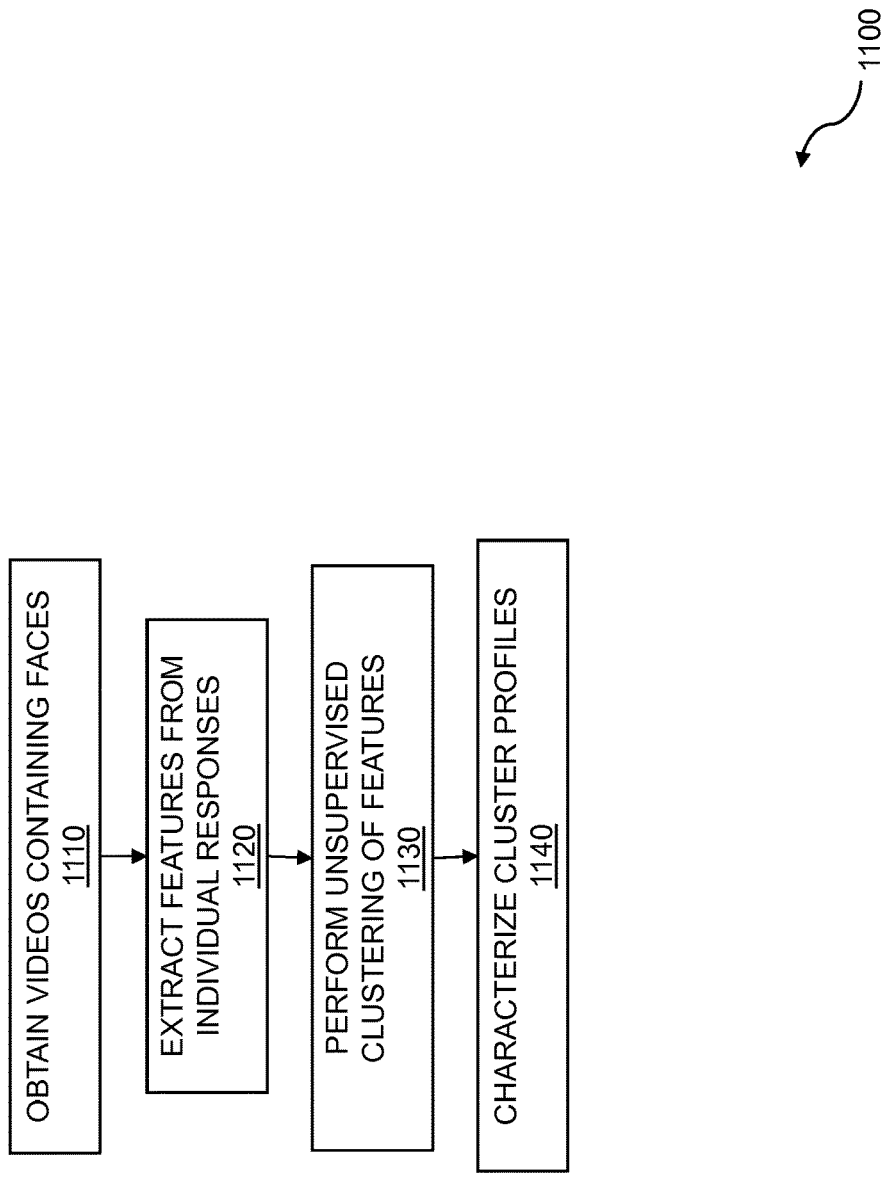
FIG. 11 is a flow diagram for the large-scale clustering of facial events.

FIG. 11 is a flow diagram for the large-scale clustering of facial events that can be used in conjunction with sporadically collected mobile affect data. The clustering and evaluation of facial events can be augmented using a mobile device, a server, semiconductor based logic, and so on. As discussed above, collection of facial video data from one or more people can include a web-based framework. The web-based framework can be used to collect facial video data from, for example, large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt-in to the video data collection. The video event can be a commercial, a political ad, an educational segment, and so on.

The flow 1100 begins with obtaining videos containing faces 1110. The videos can be obtained using one or more cameras, where the cameras can include a webcam coupled to one or more devices employed by the one or more people using the web-based framework. The flow 1100 continues with extracting features from the individual responses 1120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1100 continues with performing unsupervised clustering of features 1130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1100 continues with characterizing cluster profiles 1140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. For example, the number of smiles resulting from people viewing a humorous video can be compared to various demographic groups, where the groups can be formed based on geographic location, age, ethnicity, gender, and so on. Various steps in the flow 1100 may be changed in order, repeated, omitted, or the like without departing from the disclosed concepts. Various embodiments of the flow 1100 can be included in a computer program product embodied in a non-transitory computer readable medium that includes code executable by one or more processors. Various embodiments of the flow 1100, or portions thereof, can be included on a semiconductor chip and implemented in special purpose logic, programmable logic, and so on.

Figure 12:
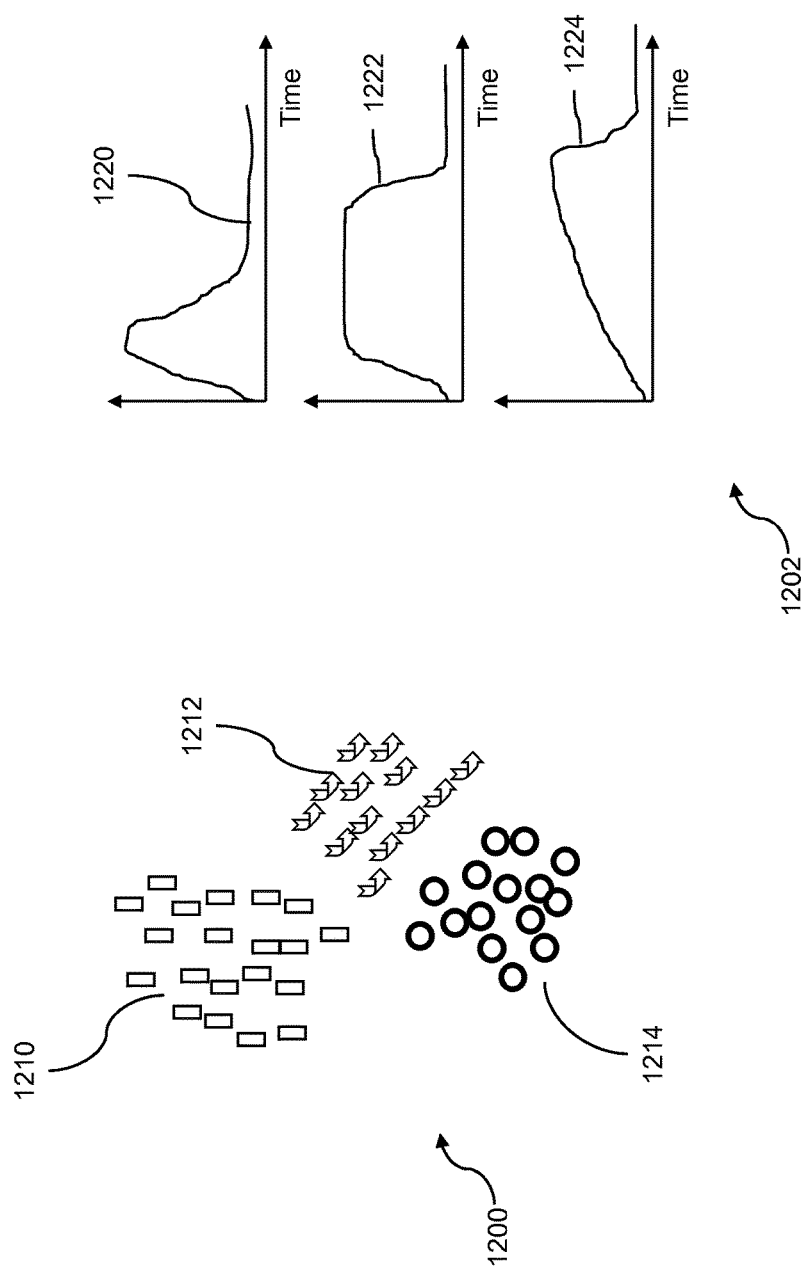
FIG. 12 shows unsupervised clustering of features and characterizations of cluster profiles.

FIG. 12 shows unsupervised clustering of features and characterizations of cluster profiles that can be used with sporadically collected mobile affect data. Features including samples of facial data can be clustered using unsupervised clustering. Various clusters can be formed, which include similar groupings of facial data observations. The example 1200 shows three clusters 1210, 1212, and 1214. The clusters can be based on video collected from people who have opted-in to video collection. When the data collected is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1202 can be generated based on the clusters that can be formed from unsupervised clustering, with time shown on the x-axis and intensity or frequency shown on the y-axis. The cluster profiles can be based on captured facial data including facial expressions, for example. The cluster profile 1220 can be based on the cluster 1210, the cluster profile 1222 can be based on the cluster 1212, and the cluster profile 1224 can be based on the cluster 1214. The cluster profiles 1220, 1222, and 1224 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 13A:
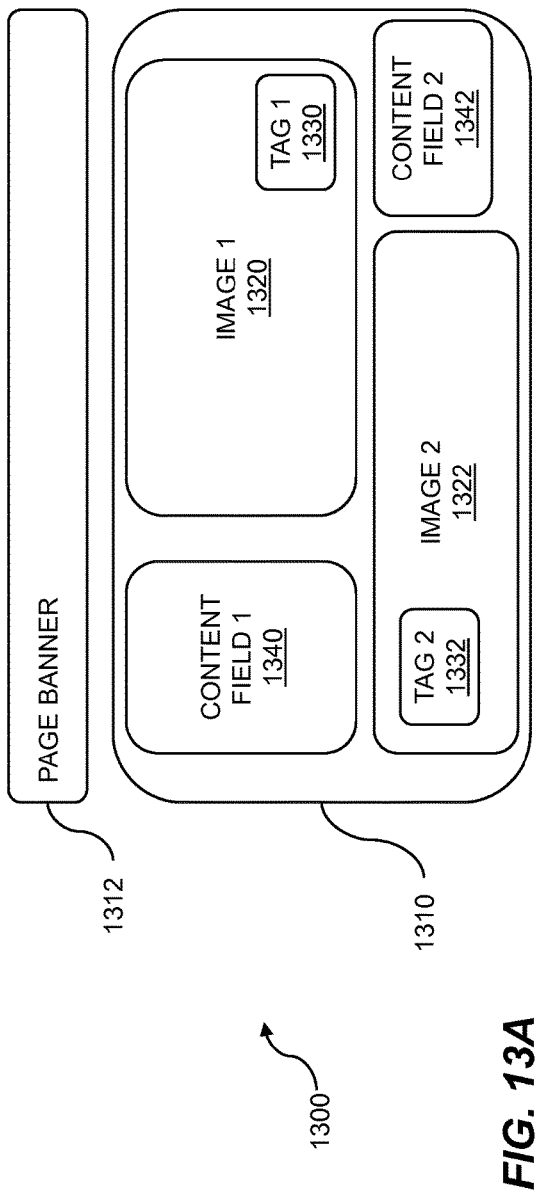
FIG. 13A shows example tags embedded in a webpage.

FIG. 13A shows example tags embedded in a webpage that can be used with sporadically collected mobile affect data. Once a tag is detected, a mobile device, a server, semiconductor based logic, etc. can be used to evaluate associated facial expressions. A webpage 1300 can include a page body 1310, a page banner 1312, and so on. The page body can include one or more objects, where the objects can include text, images, videos, audio, and so on. The example page body 1310 shown includes a first image, image 1 1320; a second image, image 2 1322; a first content field, content field 1 1340; and a second content field, content field 2 1342. In practice, the page body 1310 can contain any number of images and content fields, and can include one or more videos, one or more audio presentations, and so on. The page body can include embedded tags, such as tag 1 1330 and tag 2 1332. In the example shown, tag 1 1330 is embedded in image 1 1320, and tag 2 1332 is embedded in image 2 1322. In embodiments, any number of tags can be imbedded. Tags can also be imbedded in content fields, in videos, in audio presentations, etc. When a user mouses over a tag or clicks on an object associated with a tag, the tag can be invoked. For example, when the user mouses over tag 1 1330, tag 1 1330 can then be invoked. Invoking tag 1 1330 can include enabling a camera coupled to a user's device and capturing one or more images of the user as the user views a media presentation (or digital experience). In a similar manner, when the user mouses over tag 2 1332, tag 2 1332 can be invoked. Invoking tag 2 1332 can also include enabling the camera and capturing images of the user. In other embodiments, other actions are taken based on invocation of the one or more tags. For example, invoking an embedded tag can initiate an analysis technique, post to social media, award the user a coupon or another prize, initiate mental state analysis, perform emotion analysis, and so on.

Figure 13B:
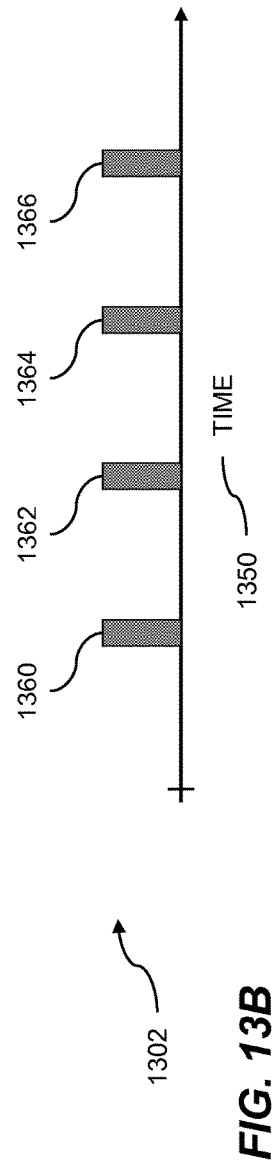
FIG. 13B shows invoking tags to collect images.

FIG. 13B shows invoking tags to collect images that can be used with sporadically collected mobile affect data. In some embodiments, the tags can invoke collection of sporadic mental state data. As stated above, a media presentation can be a video, a webpage, and so on. A video 1302 can include one or more embedded tags, such as a tag 1360, another tag 1362, a third tag 1364, a fourth tag 1366, and so on. In practice, any number of tags can be included in the media presentation. The one or more tags can be invoked during the media presentation. The collection of the invoked tags can occur over time, as represented by a timeline 1350. When a tag is encountered in the media presentation, the tag can be invoked. For example, when the tag 1360 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1360 does not enable the camera nor capture images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages, advertising messages, social media sharing, etc., and that enable the camera and image capture when invoked would be embedded in the media presentation, social media sharing, and so on. However, tags imbedded in the media presentation that are related to advertisements would not enable the camera when invoked. Various other situations of tag invocation are possible.

Figure 14:
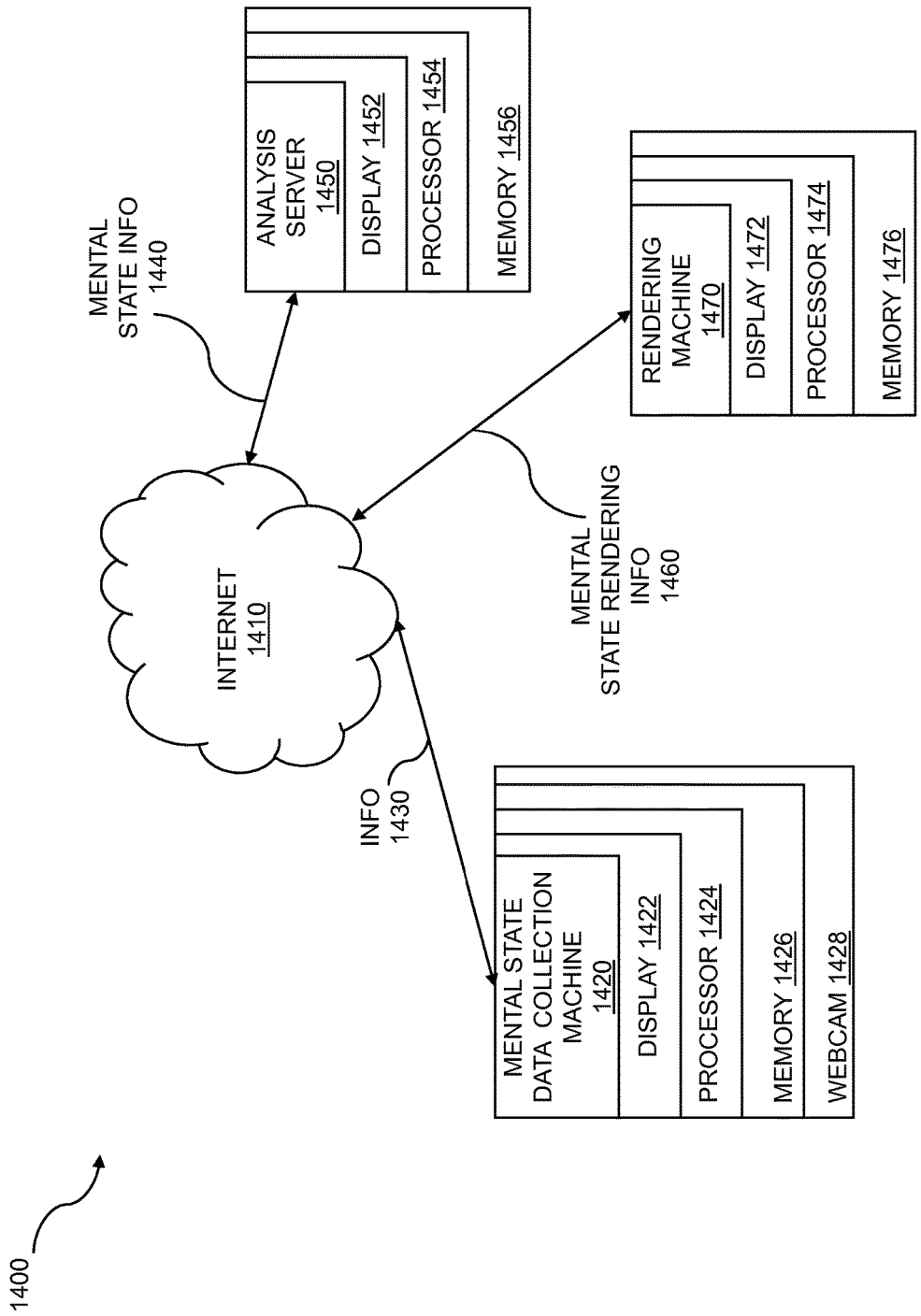
FIG. 14 is a system diagram for mental state analysis.

FIG. 14 is a system diagram for mental state analysis. A system 1400 can be used for sporadic collection of mental state data with mobile affect data. The system 1400 may include a mental state data collection machine 1420 and an analysis server 1450. The mental state data collection machine 1420 may be configured to collect the mental state data of an individual on an intermittent basis. The mental state data collection machine 1420 may include a display 1422; one or more processors 1424; a memory 1426 designed to store mental state data, instructions, and the like; and a webcam 1428. The display 1422 may be any electronic display, including but not limited to, a computer display, a laptop screen, a net-book screen, a tablet computer screen, a cell phone display, a mobile device display, a remote with a display, a television, a projector, or the like. The webcam 1428 may comprise a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that may allow image data captured to be used by an electronic system. The mental state data collection machine 1420 may be configured to transmit mental state information 1430 to a server 1450 via the Internet 1410 or another network.

The analysis server 1450 may be configured to obtain analysis of the mental state data on the individual and render an output based on the analysis of the mental state data. The analysis server 1450 may obtain mental state information 1440 from the Internet 1410 and may be configured as a web service. In some embodiments, the analysis server 1450 may send the analysis of the mental state data to another machine, such as the mental state data collection machine 1420, so that the analysis of the mental state data may be received from a web service. The analysis server 1450 may include a display 1452, one or more processors 1454, and a memory 1456 designed to store system information, instructions, and the like. The display 1452 may be any electronic display, including but not limited to, a computer display, a laptop screen, a net-book screen, a tablet computer screen, a cell phone display, a mobile device display, a remote with a display, a television, a projector, or the like. The one or more processors 1454, when executing the instructions which are stored, can be configured to analyze mental state information 1440 that may be received from the mental state data collection machine 1420. In some embodiments, the functions of the mental state data collection machine 1420 and the analysis server 1450 may be combined into a single computer. In some embodiments, the rendering of mental state analysis can occur on a different computer from the collection machine 1420 or the analysis server 1450. This computer may be a rendering machine 1470 which receives data or information 1430, mental state information 1440 from the analysis machine 1450, or both, and may be considered mental state rendering information 1460. In embodiments, the rendering machine 1470 includes one or more processors 1474 coupled to a memory 1476, and a display 1472. The rendering may include generation and display of emoticons. The rendering can include translating the mental state data into an emoji for representation of the individual. The system 1400 may include a computer program product embodied in a non-transitory computer readable medium for mental state analysis, the computer program product comprising: code for collecting mental state data of an individual on an intermittent basis wherein the mental state data includes facial data; code for interpolating mental state data in between the collecting which is intermittent; code for obtaining analysis, using one or more processors, of the mental state data on the individual; and code for rendering an output based on the analysis of the mental state data.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, mobile device, tablet, wearable computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
   collecting mental state data of an individual on an intermittent basis wherein the mental state data includes facial image data and the facial image data is collected intermittently across a plurality of devices;
   imputing additional mental state data where the mental state data is missing, wherein the imputing is based on mental state data collected from other individuals associated with the individual;
   interpolating, using one or more processors, mental state data in between the collecting which is intermittent;
   obtaining analysis of the mental state data on the individual, wherein the analysis of the mental state data is received from a web service and includes analyzing the facial image data; and
   rendering an output based on the analysis of the mental state data.

2. The method of claim 1 wherein the collecting mental state data is based on image analysis of the facial image data.

3. The method of claim 1 wherein the facial image data is obtained from a series of images of the individual.

4. The method of claim 3 further comprising identifying a second face from a second individual within the series of images.

5. The method of claim 4 further comprising tracking a face for the individual within the series of images.

6. The method of claim 5 further comprising tracking the second face within the series of images.

7. The method of claim 1 further comprising collecting other mental state data from the individual on a continuous basis.

8. The method of claim 7 wherein the other mental state data includes electrodermal activity data.

9. The method of claim 7 wherein the other mental state data includes audio voice data.

10. The method of claim 1 wherein the mental state data of an individual on an intermittent basis includes audio voice data.

11. The method of claim 1 wherein the obtaining analysis of the mental state data is based on sending a request to a web service for the analysis.

12. The method of claim 1 further comprising interpolating mental state analysis in between the collecting which is intermittent.

13. The method of claim 1 wherein the facial image data is collected intermittently when the individual is looking in a direction of a camera.

14. The method of claim 13 further comprising performing face detection to determine when the individual is looking in the direction of the camera.

15. The method of claim 14 wherein the face detection is based on image classifiers.

16. The method of claim 1 further comprising comparing the mental state data against a plurality of mental state event temporal signatures.

17. The method of claim 1 further comprising filtering out faces of one or more other people to determine when the individual is looking in a direction of a camera.

18. The method of claim 1 further comprising determining contextual information.

19. The method of claim 18 wherein the contextual information is based on one or more of skin temperature or accelerometer data.

20. The method of claim 18 wherein the contextual information is based on one or more of a photograph, an email, a text message, a phone log, or GPS information.

21. The method of claim 1 further comprising translating the mental state data into an emoji for representation of the individual.

22. The method of claim 1 further comprising interpolating mental state analysis in between the collecting which is intermittent; collecting other mental state data, including electrodermal activity data, from the individual on a continuous basis; imputing additional mental state data where the mental state data is missing; filtering out faces of one or more other people to determine when an individual is looking in a direction of a camera; determining contextual information based on accelerometer data; and sending a request to a web service for the analysis where the analysis of the mental state data is received from a web service.

23. The method of claim 1 further comprising sending one or more of the mental state data, a subset of the mental state data, or an initial analysis of the mental state data to the web service.

24. The method of claim 23 wherein the sending is accomplished on a periodic basis.

25. The method of claim 1 further comprising inferring mental states based on the mental state data which was collected.

26. A computer program product embodied in a non-transitory computer readable medium for mental state analysis, the computer program product comprising code which causes one or more processors to perform operations of:
   collecting mental state data of an individual on an intermittent basis wherein the mental state data includes facial image data and the facial image data is collected intermittently across a plurality of devices;
   imputing additional mental state data where the mental state data is missing, wherein the imputing is based on mental state data collected from other individuals associated with the individual;
   interpolating mental state data in between the collecting which is intermittent;
   obtaining analysis of the mental state data on the individual, wherein the analysis of the mental state data is received from a web service and includes analyzing the facial image data; and
   rendering an output based on the analysis of the mental state data.

27. A system for mental state analysis comprising:
   a memory for storing instructions;
   one or more processors attached to the memory wherein the one or more processors are configured to:
      collect mental state data of an individual on an intermittent basis wherein the mental state data includes facial image data and the facial image data is collected intermittently across a plurality of devices;
      impute additional mental state data where the mental state data is missing, wherein the additional mental state data is based on mental state data collected from other individuals associated with the individual;
      interpolate mental state data in between the collecting which is intermittent;
      obtain analysis of the mental state data on the individual, wherein the analysis of the mental state data is received from a web service and includes analyzing the facial image data; and
render an output based on the analysis of the mental state data.

28. The method of claim 1 wherein the other individuals are geographically nearby the individual.

29. The method of claim 1 wherein the other individuals are connected with the individual on a computerized social network.

* * * * *